US010537743B2

(12) United States Patent
Smyth et al.

(10) Patent No.: US 10,537,743 B2
(45) Date of Patent: Jan. 21, 2020

(54) IMPLANT INFECTION CONTROL

(71) Applicant: Cochlear Limited, Macquarie University, NSW (AU)

(72) Inventors: Daniel Smyth, Dublin (IE); Claudiu G. Treaba, New York, NY (US); Fysh Dadd, Lane Cove (AU); Kristien Johanna Marie Verhoeven, Mechelen (BE); Jonathon Kirk, New York, NY (US); Marcus Andersson, Mölnlycke (SE)

(73) Assignee: Cochlear Limited, Macquarie University (AU)

( * ) Notice: Subject to any disclaimer, the term of this patent is extended or adjusted under 35 U.S.C. 154(b) by 589 days.

(21) Appl. No.: 15/158,136

(22) Filed: May 18, 2016

(65) Prior Publication Data
US 2017/0239473 A1 Aug. 24, 2017

Related U.S. Application Data

(60) Provisional application No. 62/299,128, filed on Feb. 24, 2016.

(51) Int. Cl.
*H04R 25/00* (2006.01)
*A61N 1/375* (2006.01)

(52) U.S. Cl.
CPC ........... *A61N 1/375* (2013.01); *H04R 25/606* (2013.01); *H04R 25/65* (2013.01)

(58) Field of Classification Search
CPC ............... A61N 1/36038; A61N 1/375; H04R 25/00–75; H04R 25/606;
(Continued)

(56) References Cited

U.S. PATENT DOCUMENTS 7,054,691 B1 * 5/2006 Kuzma ................ H04R 25/606
607/36
9,125,973 B2 9/2015 Bui et al.
(Continued)

FOREIGN PATENT DOCUMENTS

CN 104519838 A 4/2015
WO 2005058414 A1 6/2005
(Continued)

OTHER PUBLICATIONS

"Colatamp G, Resorbable Gentamicin Collagen Haemostat", Tribute Pharmaceuticals, Retrieved from http://ams.body1.com/collatampg/downloads/Collatamp%20Order%20Form%20Eng_FINAL.pdf on May 18, 2016, 1 pg.
(Continued)

*Primary Examiner* — Thaddeus B Cox
(74) *Attorney, Agent, or Firm* — Edell, Shapiro & Finnan, LLC

(57) ABSTRACT

Embodiments presented herein are generally directed to a perioperative implant cover configured to cover at least a portion of an implantable component during portions of the perioperative period (i.e., preoperative, intraoperative, and postoperative phases of surgery) in which the implantable component is susceptible to bacteria contamination. By covering the implantable component during these portions of the perioperative period, the cover reduces the possibility of bacteria contamination and subsequent perioperative colonization.

36 Claims, 15 Drawing Sheets

(58) Field of Classification Search
CPC ........... H04R 2225/00–83; H04R 2460/00–17; H04R 25/60–606; H04R 25/65; H04R 2225/025; H04R 2225/67; H04R 2225/77; H04R 2460/13; H04R 2460/17; A61F 2/0031; A61F 2/0036; A61F 2/0045; A61F 2/0063

See application file for complete search history.

(56) References Cited

U.S. PATENT DOCUMENTS

| | | | |
|---|---|---|---|
| 2005/0267564 A1 | 12/2005 | Tang et al. | |
| 2006/0025649 A1* | 2/2006 | Smith | A61B 17/06066 600/30 |
| 2007/0100464 A1* | 5/2007 | Meulink | A61F 2/0095 623/23.46 |
| 2009/0012594 A1 | 1/2009 | Gibson | |
| 2010/0204551 A1* | 8/2010 | Roche | A61B 5/0031 600/301 |
| 2010/0278894 A1 | 11/2010 | Burgmeier | |
| 2012/0232615 A1 | 9/2012 | Barolat et al. | |
| 2013/0066339 A1* | 3/2013 | Hod | A61B 17/00234 606/139 |
| 2013/0096366 A1* | 4/2013 | Bervoets | A61N 1/36036 600/25 |
| 2014/0370067 A1 | 12/2014 | Margraf et al. | |

FOREIGN PATENT DOCUMENTS

| | | |
|---|---|---|
| WO | 2014137454 A1 | 9/2014 |
| WO | 2015/132158 A1 | 9/2015 |

OTHER PUBLICATIONS

"Medtronic TYRX(TM) Neuro Absorbable Antibactierial Envelope now Available for Use with Implantable Neurostimulators," Medtronic, Oct. 8, 2015, http://newsroom.medtronic.com/phoenix.zhtml?c=251324&p=irol-newsArticle&id=2095576, pp. 1-2.

International Search Report and Written Opinion in corresponding International Application No. PCT/IB2017/050788, dated May 19, 2017, 10 pages.

Extended European Search Report in counterpart European Application No. EP17755899, dated Nov. 13, 2019, 6 pages.

* cited by examiner

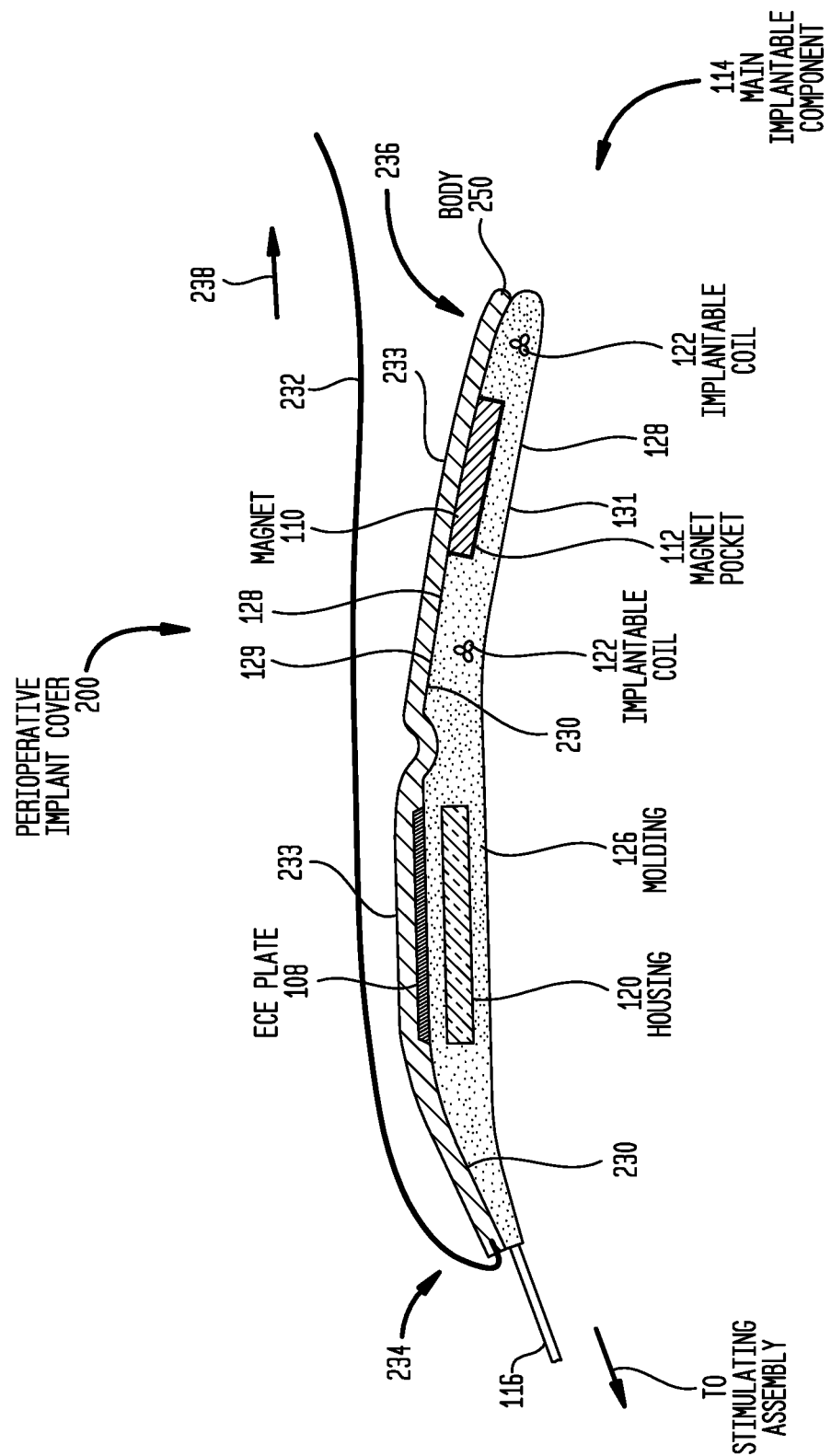

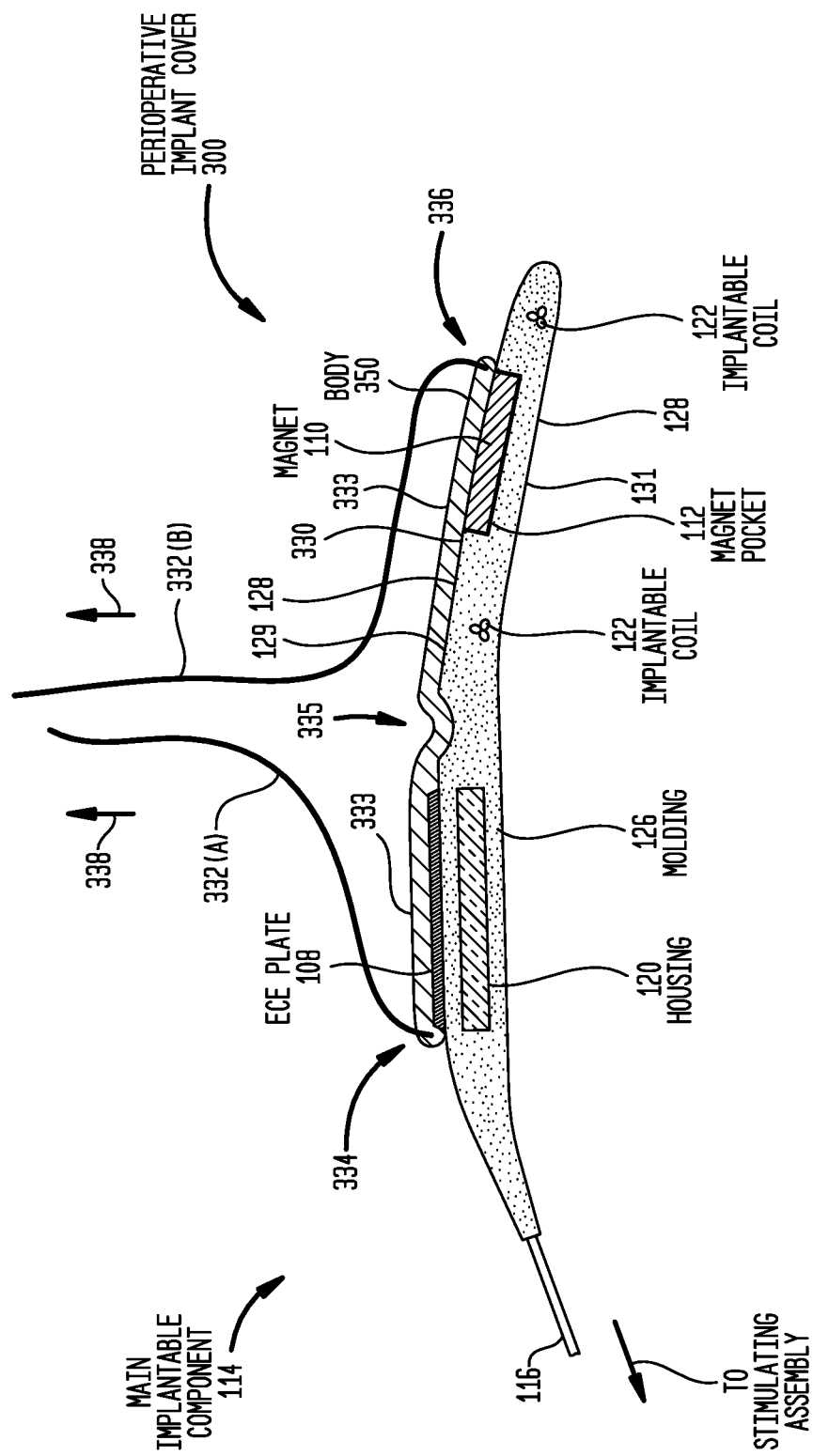

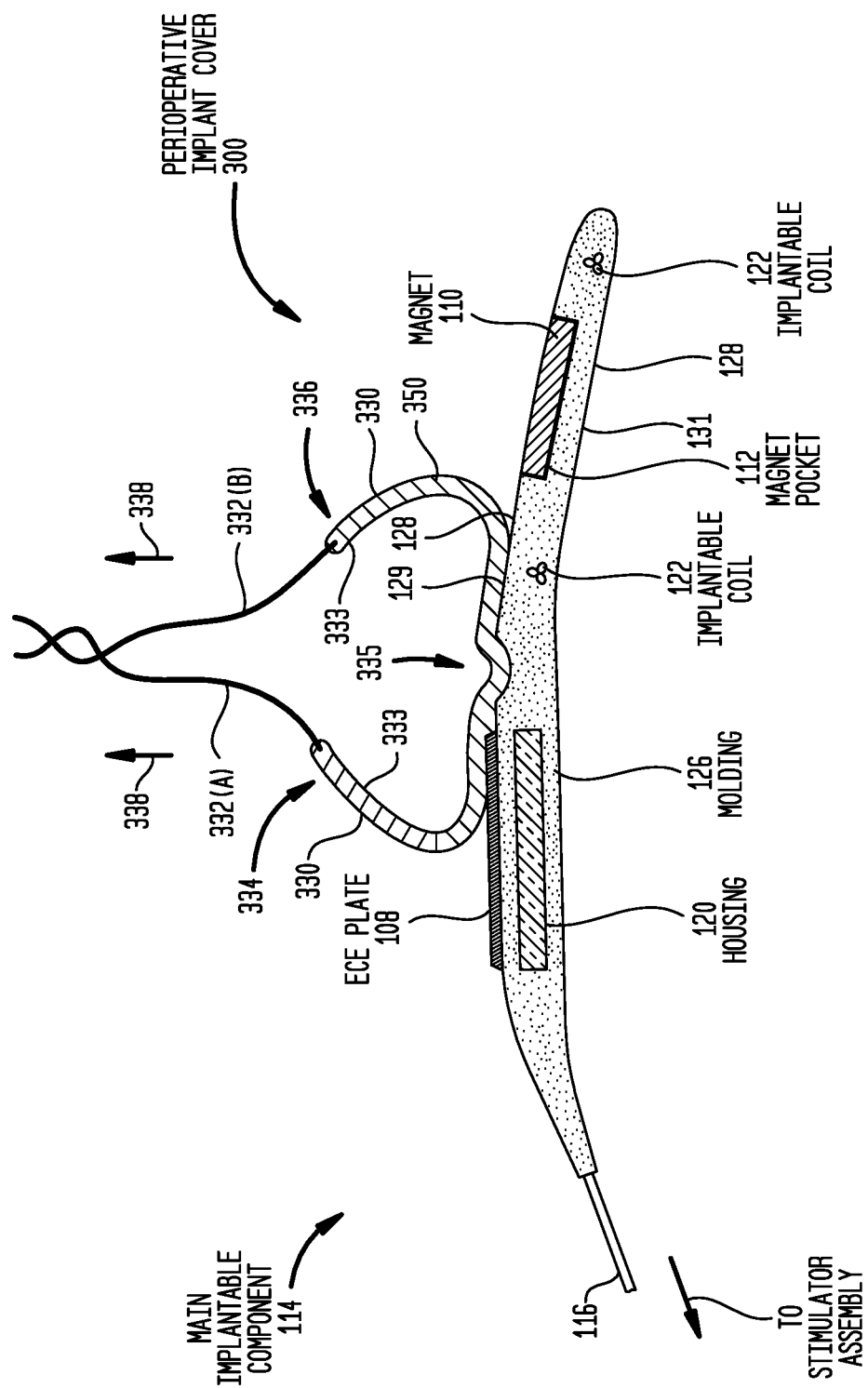

602 — IMPLANTING AN IMPLANTABLE COMPONENT OF AN IMPLANTABLE MEDICAL DEVICE INTO A RECIPIENT, WHEREIN A PERIOPERATIVE IMPLANT COVER COMPRISING A BODY IS DISPOSED ON AT LEAST A PORTION OF A SURFACE OF THE IMPLANTABLE COMPONENT DURING IMPLANTATION OF THE IMPLANTABLE COMPONENT INTO THE RECIPIENT

604 — REMOVING THE PERIOPERATIVE IMPLANT COVER FROM THE RECIPIENT AFTER THE IMPLANTABLE COMPONENT IS FULLY IMPLANTED IN RECIPIENT

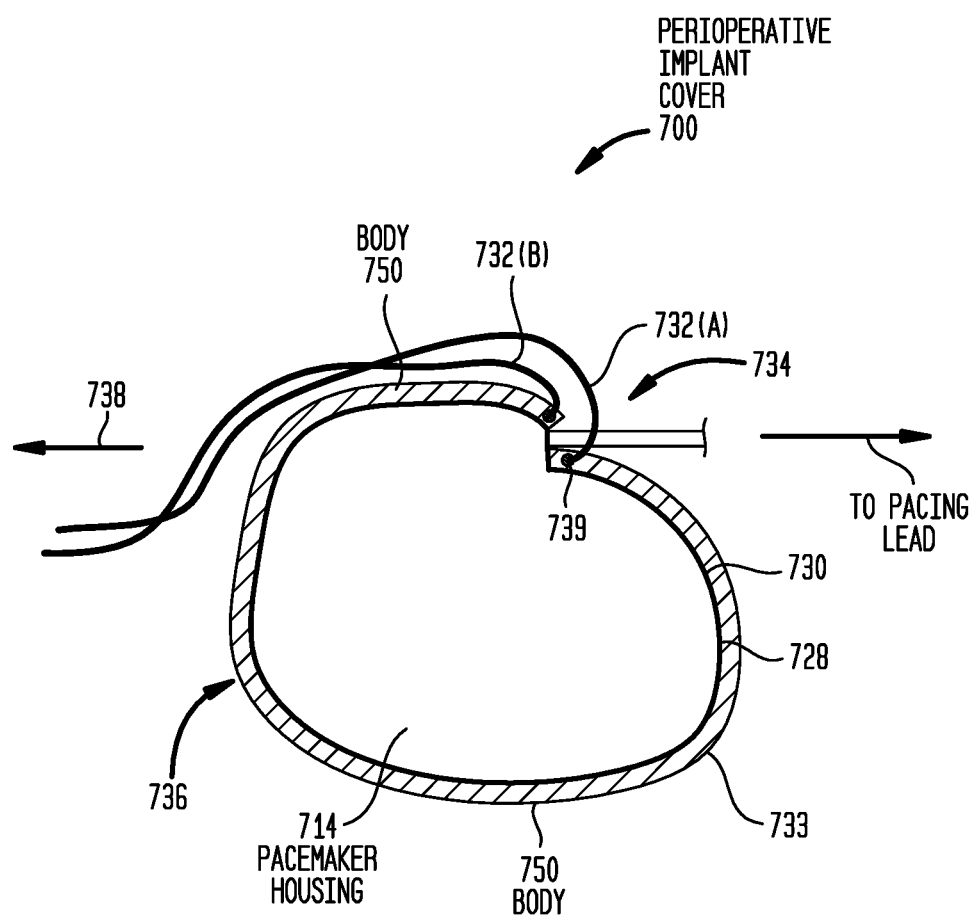

IMPLANT INFECTION CONTROL

CROSS REFERENCE TO RELATED APPLICATIONS

This application claims priority to U.S. Provisional Application No. 62/299,128 entitled "Implant Infection Control," filed Feb. 24, 2016, the content of which is hereby incorporated by reference herein.

BACKGROUND

Field of the Invention

The present invention relates generally to implantable medical devices.

Related Art

Medical device systems having one or more implantable components, generally referred to herein as implantable medical device systems, have provided a wide range of therapeutic benefits to recipients over recent decades. In particular, partially or fully-implantable medical device systems including active or passive (non-active) implantable components, such as hearing prostheses (e.g., bone conduction devices, mechanical stimulators, cochlear implants, etc.), implantable cardioverter defibrillators (ICDs), implantable pacemakers, functional electrical stimulation devices or other neurostimulators, pain management implants, implantable drug or insulin pumps, mammary prosthesis/breast implants, cosmetic or reconstructive implants and prosthetics, etc., have been successful in performing life saving and/or lifestyle enhancement functions for a number of years.

The types of implantable medical device systems and the ranges of functions performed thereby have increased over the years. For example, many implantable medical device systems now often include one or more instruments, apparatus, sensors, processors, controllers or other functional mechanical or electrical components that are permanently or temporarily implanted in a recipient. These functional components perform diagnosis, prevention, monitoring, treatment or management of a disease or injury or symptom thereof, or to investigate, replace or modify of the anatomy or of a physiological process.

SUMMARY

In one aspect an implantable medical device system is provided. The implantable medical device system comprises: an implantable component for implantation into a recipient; and a perioperative implant cover comprising a body disposed on at least a portion of a surface of the implantable component during implantation of the implantable component into the recipient, wherein the perioperative implant cover includes one or more in situ removal features enabling the perioperative implant cover to be removed from the surface of the implantable component after implantation in the recipient.

In another aspect a perioperative implant cover is provided. The perioperative implant cover comprises: a cover body having a first and second opposing surfaces, wherein the first surface is configured to be attached to an outer surface of an implantable component of an implantable medical device; and one or more removal features that enable the first surface of the cover body to be separated from the outer surface of the implantable component for withdrawal of the perioperative implant cover from the recipient.

In another aspect a method is provided. The method comprises: implanting an implantable component of an implantable medical device into a recipient, wherein a perioperative implant cover comprising a body is disposed on at least a portion of a surface of the implantable component during implantation of the implantable component into the recipient; and removing the perioperative implant cover from the recipient after the implantable component is fully implanted in the recipient.

BRIEF DESCRIPTION OF THE DRAWINGS

Embodiments of the present invention are described herein in conjunction with the accompanying drawings, in which:

FIG. 2A is a cross-sectional side view of another perioperative implant cover in accordance with embodiments of the present invention shown with a cochlear implant;

FIG. 3A is a cross-sectional side view of another perioperative implant cover in accordance with embodiments of the present invention shown with a cochlear implant;

FIG. 3B is a cross-sectional side view of the perioperative implant cover of FIG. 3A illustrating a first technique for removal of the cover from the cochlear implant;

FIG. 6 is a flowchart of a method in accordance with embodiments of the present invention; and FIG. 7 is a cross-sectional side view of a perioperative implant cover in accordance with embodiments of the present invention shown with a pacemaker housing.

DETAILED DESCRIPTION

Figure 1A:
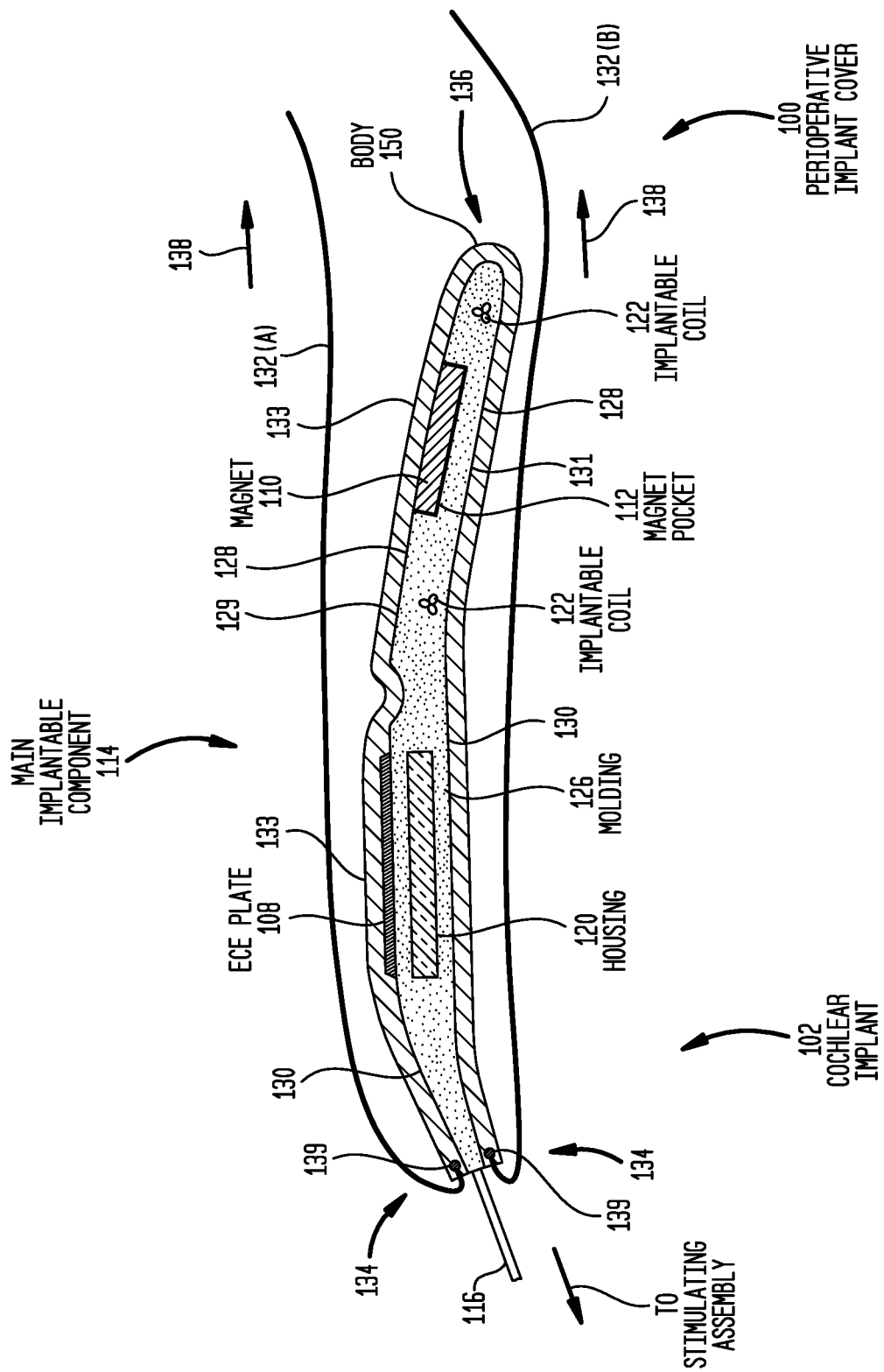
FIG. 1A is a cross-sectional side view of a perioperative implant cover in accordance with embodiments of the present invention shown with a cochlear implant.

Infections occur in a percentage of recipients of different types of implantable medical devices, but the percentage varies for different types of devices. The severity and causes of these infections may also vary, but the applicant has determined that cochlear implant systems are primarily impacted by "biofilm" infections. A biofilm is a cluster of bacteria that develops a protective extracellular matrix which is difficult to treat using standard infection treatment regimens (e.g., systemic or local antibiotics). The applicant has also determined that a sizeable portion of biofilm infections can be attributed to perioperative colonization of the implantable component by nosocomial (hospital) bacteria (e.g., bacteria falling onto or being transferred to the implantable component before or during the implantation surgery). For example, bacteria may be introduced by surgical instruments and individuals in the operating room where, the longer the wound is open the greater the number of bacteria introduced into the wound, and the more individuals in the operating room, the greater the amount of bacteria introduced into the wound.

Biofilm infections are a primary cause of explantation (removal of the implantable component from the recipient), even if the eventual explantation happens many years later. For example, it is possible that bacteria can colonize and possibly cause no issues (e.g., sub-clinical infection or no clinical symptoms of infection) until a subsequent triggering event, such as the arrival of pathogenic bacteria to the biofilm, the recipient having a compromised immune state from an unrelated sickness, trauma to the area of the implant, etc. The triggering event then causes clinical symptoms of an infection to appear.

Since, as noted above, efforts to treat biofilm infections with pharmaceuticals or chemicals alone are difficult, some medical practitioners have attempted to use surgical debridement (mechanical removal) of the biofilm to control infections. However, thorough/complete debridement of biofilms on the complicated geometry and sensitive surfaces of many implantable components is challenging and rarely effective without chronic systemic antibiotic treatment. As such, a large number of biofilm infections on implantable components of medical devices result in explantation and subsequent re-implantation after a sufficient healing period.

Biofilm in the presence of an implantable component typically results in colonization of the implantable component surface. The healthy tissue surrounding the implantable component in the early stages of an implant associated infection is not immuno-compromised and therefore is capable of defending itself from infection. However, in later stage infections when the tissue has been damaged by long exposure to cytokines and inflammation, the tissue is more vulnerable.

As such, embodiments presented herein are generally directed to a perioperative implant cover configured to cover at least a portion of an implantable component during portions of the perioperative period (i.e., preoperative, intraoperative, and postoperative phases of surgery) in which the implantable component is susceptible to bacteria contamination. By covering at least portions of the implantable component during these portions of the perioperative period, the cover reduces the possibility of bacterial contamination and related colonization.

As described further below, a perioperative implant cover in accordance with embodiments presented herein is configured such that bacteria introduced into the surgical wound, or into the healing implant site following surgery, will collect on the cover and not on the covered surface(s) of the implantable component. As described further below, perioperative implant covers in accordance with embodiments presented herein also include one or more in situ removal features enabling removal of the cover after the covered implantable component is implanted in a recipient, that is, after the implantable component is placed and/or secured at its final implanted position. In certain examples, the removal feature(s) enable removal of the cover in a manner that eliminates or reduces the transfer of bacteria from the cover to the implantable component.

The perioperative implant cover may be removed at the end of the implantation surgery (e.g., final step of intraoperative phase) or some time after completion of the implantation surgery (e.g., several days/weeks after the implantation surgery during the postoperative phase). As such, the previously covered surface(s) of the implantable component are only exposed in a reduced risk environment, such as no open wound (e.g., only a small percutaneous opening) or an open wound that is exposed for only a very short period of time.

A perioperative implant cover in accordance with embodiments presented herein may be configured such that the cover folds back onto itself during the removal process in order to trap the bacteria on the cover and further protect the surface of the implantable component from bacteria contamination. Removal of the perioperative implant cover at the end of the implantation surgery, or some time after completion of the implantation surgery, results in a fully implanted implantable component having one or more surface regions that have not been contaminated by bacteria present in the operating room/surgical theater.

Perioperative implant covers in accordance with embodiments presented herein are described herein primarily in connection with one type of implantable medical device system, namely a cochlear implant system comprising an internal (implantable) component. It is to be appreciated that embodiments of the present invention may be implemented in any partially or fully-implantable medical device systems including active or passive (non-active) implantable components, such as hearing prostheses (e.g., bone conduction devices, mechanical stimulators, cochlear implants, etc.), implantable cardioverter defibrillators (ICDs), implantable pacemakers, functional electrical stimulation devices or other neurostimulators, pain management implants, implantable drug or insulin pumps, mammary prosthesis/breast implants, cosmetic or reconstructive implants and prosthetics, etc.

In general, perioperative implant covers in accordance with embodiments presented herein are thin sterile elements that protect at least a portion of an implantable component from bacterial infection during the perioperative period. However, the perioperative implant covers in accordance with embodiments presented herein may have a number of different arrangements.

Figure 1B:
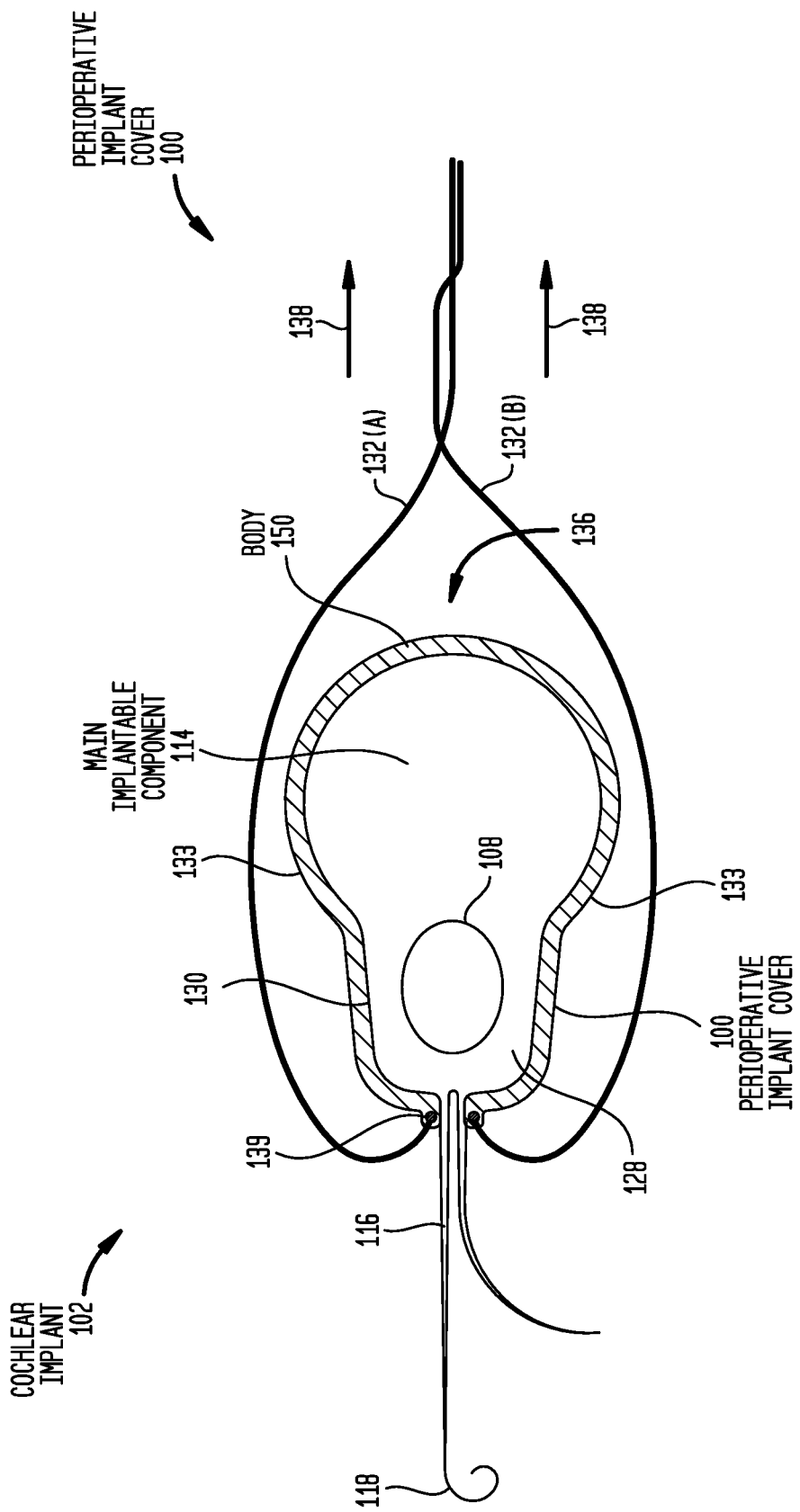
FIG. 1B is a cross-sectional top view of the perioperative implant cover of FIG. 1A shown with a cochlear implant.
Figure 1C:
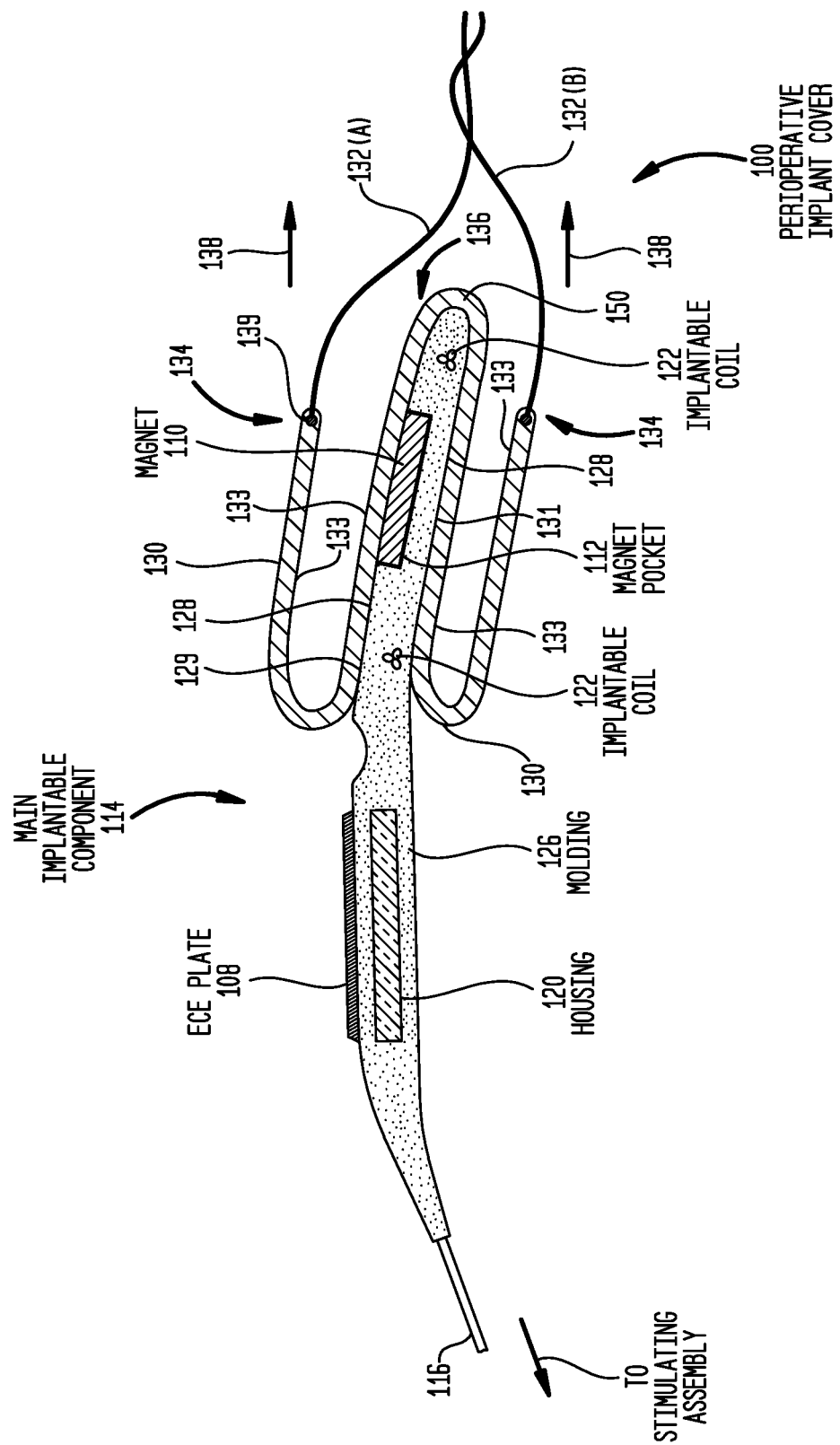
FIG. 1C is a cross-sectional side view of the perioperative implant cover of FIG. 1A during removal of the cover from the cochlear implant.
Figure 1D:
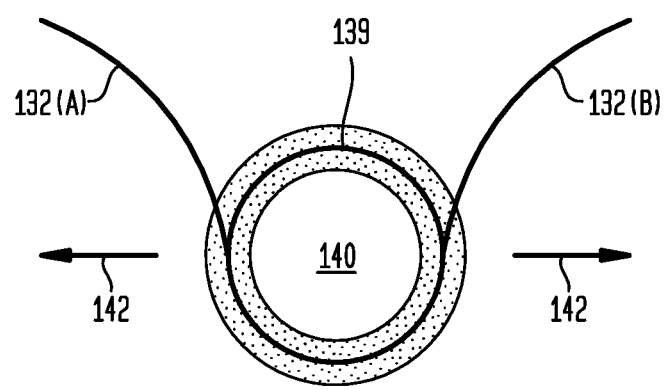
FIG. 1D and FIG. 1E are cross-sectional views of a distal end of the perioperative implant cover of FIG. 1A during removal of the cover from the cochlear implant.
Figure 1E:
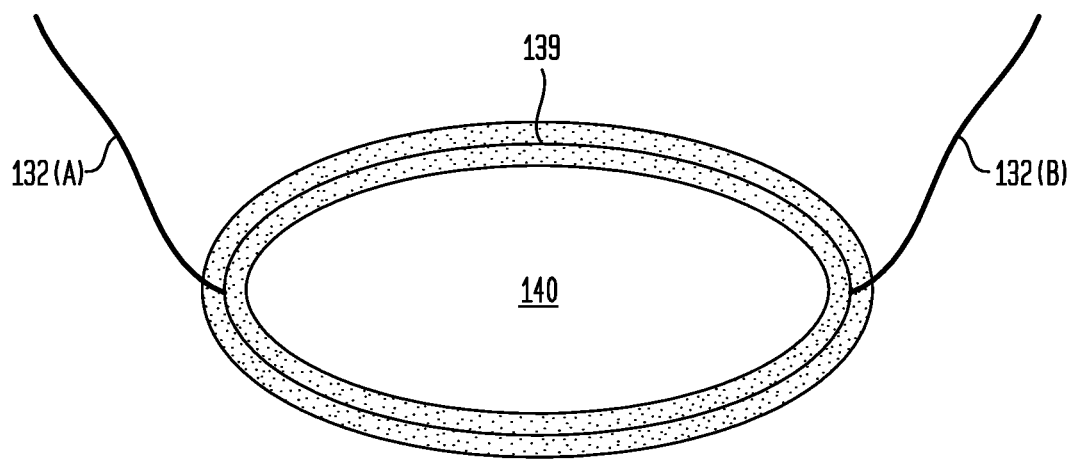

For example, FIGS. 1A-1E are a series of diagrams illustrating a perioperative implant cover 100 in accordance with embodiments of the present invention for use with a cochlear implant 102. In particular, FIG. 1A is a cross-sectional side view of the perioperative implant cover 100, while FIG. 1B is a cross-sectional top view of the perioperative implant cover 100. FIG. 1C is a cross-sectional side view of the perioperative implant cover 100 during removal of the cover from the cochlear implant 102. FIG. 1D is a cross-sectional view of a distal end of the perioperative implant cover 100 prior to removal of the cover from the cochlear implant 102, while FIG. 1E is a cross-sectional view of a distal end of the perioperative implant cover 100 during removal of the cover from the cochlear implant 102. For context, a brief overview of the cochlear implant 102 is provided before describing further details of the perioperative implant cover 100.

Referring first to FIG. 1A, the cochlear implant 102 comprises an implant body or main implantable component 114, a lead region 116, and an elongate intra-cochlear stimulating assembly 118 (shown in FIG. 1B). The main implantable component 114 comprises a stimulator unit and an internal receiver/transceiver unit, sometimes referred to herein as transceiver unit, both of which are disposed in a hermetically sealed housing 120. The main implantable component 114 also includes an extra-cochlear electrode plate 108 and an internal/implantable coil 122 that is connected to the transceiver unit located in the housing 120. The main implantable component 114 further comprises a flexible molding 124 (e.g., silicone molding) that encases the housing 120 and the implantable coil 122.

The main implantable component 114 also comprises a magnet 110 fixed relative to the internal coil 122. In the arrangement of FIG. 1A, the magnet 110 is located in an opening or "pocket" 112 formed in the flexible molding 124.

In the examples of FIGS. 1A-1E, the main implantable component 114 is implanted in a recipient adjacent to the recipient's skull and under the recipient's skin/tissue layer(s) (i.e., in a small "pocket" formed in the recipient's bone). As described further below, the perioperative implant cover 100 is attached to the main implantable component 114 before implantation, and is configured to remain attached thereto during the implantation surgery. For ease of illustration, the recipient's skull bone and skin/tissue have been omitted from FIGS. 1A-1E.

The perioperative implant cover 100 has a body 150 that is configured to cover at least a portion of the main implantable component 114 while the cochlear implant 102 is implanted in the recipient. In the examples of FIGS. 1A-1E, the main implantable component 114 includes an outer surface 128 that includes opposing first and second surfaces 129 and 131. When the main implantable component 114 is fully implanted adjacent to the recipient's skull, the first surface 129 is an "upper" or "skin-facing" surface, while the second surface 131 is a "lower" or "bone-facing" surface 131. The perioperative implant cover body (cover body) 150 of FIGS. 1A-1E is in the form of a sheath or pouch that substantially surrounds the outer surface 128 of the main implantable component 114, including substantially all of both the skin-facing surface 129 and the bone-facing surface 131.

More specifically, the cover body 150 includes a first surface 130 (e.g., an interior or device-facing surface) that defines an interior cavity in which the main implantable component 114 is positioned. The first surface 130 is attached to the outer surface 128 of the main implantable component 114. In general, the first surface 130 is attached to the outer surface 128 of the main implantable component 114 such that cover body 150 remains on the outer surface during implantation of the main implantable component 114 into the recipient. In certain embodiments, the first surface 130 is attached to the outer surface 128 as a result of the elastic nature of the cover material and/or by being close fitting/confirming to the shape of the main implantable component 114. In further embodiments, the first surface 130 of the perioperative implant cover body 150 is attached to the outer surface 128 via an adhesive (e.g., silicone adhesive) or hook-and-loop fasteners. In other examples, the first surface 130 is attached to the outer surface 128 through surface interactions (e.g., friction). In certain such examples, the first surface 130 may be textured (e.g., include dimples/protrusions, ridges, concavities, etc.) to increase the friction between the first surface 130 and the outer surface 128.

In further embodiments, features of the main implantable component 114 may be used to retain the body 150 of the perioperative implant cover 100 on the main implantable component and/or a magnet may be disposed in the cover body 150. In one such embodiment, the magnet in the perioperative implant cover body 150 is magnetically coupled to the magnet 110 in the main implantable component 114 or another portion of the main implantable component 114 to retain the position of the cover during implantation.

In certain embodiments, the perioperative implant cover 100 (i.e., the cover body 150) is attached to the main implantable component 114 during, for example, a manufacturing process. As such, the perioperative implant cover 100 may be attached in a controlled and sterile environment to ensure that no bacteria are sealed between the cover and the main implantable component 114. In such examples, the main implantable component 114 and attached perioperative implant cover 100 may then be packaged together in sterile packaging material. Alternatively, the perioperative implant cover 100 may be attached to the main implantable component 114 prior to, or at the beginning of an implantation surgery in a sterile manner or in a sterile field.

As noted above, once the main implantable component 114 is implanted in the recipient at its final position/location, the perioperative implant cover 100 is configured for removal from the main implantable component 114 (and the recipient) in a manner that eliminates or reduces the transfer of bacteria from the cover to the implantable component. That is, the perioperative implant cover 100 includes one or more structural features that enable a medical practitioner (e.g., surgeon) to separate the cover the implantable component and withdraw the cover from the recipient without transferring bacteria from the perioperative implant cover 100 to the surface of the main implantable component 114.

To enable removal of the perioperative implant cover 100, the perioperative implant cover includes one or more removal features. These removal features are sometimes referred to herein as "in situ" removal features because they enable removal of the perioperative implant cover 100 without significantly disturbing the implantable component when it is fully implanted (i.e., located at its final position in the recipient). As a result, the in situ removal features enable the perioperative implant cover 100 to be removed from the main implantable component 114 and the recipient at end of the implantation surgery, namely either as final step, or one of the final steps, of the intraoperative phase just before the wound is closed or during the postoperative phase, such as three (3) days after the implantation surgery (e.g., percutaneous removal a couple of days after the surgery). This minimizes and/or eliminates a time period during which the surface of the implantable component is exposed to any bacteria present in the surgical theater.

In accordance with examples presented herein in which the perioperative implant cover 100 is removed during the postoperative phase, no second surgery is envisaged. Instead, the perioperative implant cover 100 may be withdrawn through a percutaneous opening (e.g., a fistula/cannula or small incision) remote from the implantable component.

A perioperative implant cover in accordance with embodiments of the present invention may include a number of different removal features in various combinations. FIGS. 1A-1E illustrate an arrangement in which the removal features include two percutaneous draw or retracting cords/strings 132(A) and 132(B) that are each mechanically coupled to (e.g., attached to, embedded in, etc.) a distal end 134 of the perioperative implant cover body 150. In this example, the distal end 134 is the end of the perioperative implant cover body 150 that is located farthest away from a percutaneous opening (not shown) through which the perioperative implant cover 100 is to be withdrawn from the recipient, while the proximal end 136 of the cover body 150 is the end that is located closest to the percutaneous opening.

The retracting cords 132(A) and 132(B) may have different arrangements and may be formed from, for example, metal, polymers, etc. For example, the retracting cords 132(A) and 132(B) may be percutaneous elements (i.e., elements that extend through the percutaneous removal opening) or may be subcutaneous elements (i.e., elements that terminate subcutaneously for subsequent retrieval by the medical practitioner). In certain examples, the retracting cords 132(A) and 132(B) may have a radiopaque marker that is externally detectable by, for example, medical imaging techniques (e.g., X-ray, Ultraviolet (UV), infrared (IR), etc.). In further examples, the retracting cords 132(A) and 132(B) may be impregnated or coated with a non-fouling material, an antibacterial material, biocide, etc. The retracting cords 132(A) and 132(B) may be formed from a different material than the cover body 150 or may be continuations of the material forming the cover body 150. Additionally, the retracting cords 132(A) and 132(B) may be coated wires or wire coated strings.

As described elsewhere herein, the retracting cords 132(A) and 132(B) are used to remove the perioperative implant cover 100 through a percutaneous removal opening. The percutaneous removal opening may be an incision in the recipient's skin tissue, or an opening formed by a withdrawal tube/cannula extending through the recipient's skin tissue. Such a withdrawal tube may be formed, for example, from metal or a hard thermoplastic, or may be a relatively soft material through which the retracting cords 132(A) and 132(B) and perioperative implant cover 100 may be withdrawn.

When it is time to remove the perioperative implant cover 100 from the cochlear implant 102, a medical practitioner (e.g., surgeon) pulls the retracting cords 132(A) and 132(B) towards the proximal end 136 of the cover body 150 (i.e., in the general direction illustrated in FIGS. 1A-1C by arrows 138). As shown in FIGS. 1D and 1E, the actuation (pulling action) of the retracting cords 132(A) and 132(B) exerts a force on an opening string 139 that is located at the distal end 134 of the perioperative implant cover body 150 and mechanically connected to the retracting cords 132(A) and 132(B).

More specifically, FIG. 1D illustrates that the distal end 134 of the perioperative implant cover body 150 includes an aperture 140 that is enclosed around one of the lead region 116 or the distal end of the main implantable component 114. For ease of illustration, the element positioned within aperture 140 (i.e., either the lead region 116 or the distal end of the main implantable component 114) has been omitted from FIGS. 1D and 1E. When the medical practitioner (e.g., surgeon) actuates (pulls) the retracting cords 132(A) and 132(B) towards the proximal end of the perioperative implant cover body 150, the retracting cords in turn place an opening (pulling) force on the opening string 139 to increase the size of the aperture 140, as represented by arrows 142. The increased aperture size, as shown in FIG. 1E, enables the cover body 150 to be pulled back over the larger geometry of the main implantable component 114.

Returning to FIG. 1C, after aperture 140 has the increased size, and in response to additional force on the retracting cords 132(A) and 132(B), the first surface 130 of the cover body 150 peels away from the outer surface 128 of the main implantable component 114. As the distal end 134 of the perioperative implant cover body 150 is pulled in direction 138, the proximal end 136 remains stationary and attached to the main implantable component 114 until the rest of the cover body 150 is removed, at which time the proximal end 136 also detaches from implantable component 114.

The perioperative implant cover body 150 has a structure (e.g., formed from type of material, a thickness, etc.) that, when coupled with the fact that the proximal end 136 remains stationary, causes the perioperative implant cover body 150 to fold back over itself during removal. In other words, during the removal process, the first surface 130 becomes the outward facing surface, while different portions of a second surface (e.g., initially outer or outward-facing) surface 133 of the cover body 150 approach one another. As a result, any surface adhered bacteria on outer surface 133 are trapped within the perioperative implant cover body 150 between adjacent portions of the outer surface 133 and are withdrawn from the recipient along with the cover body 150. This ensures substantial protection of the surface of the main implantable component 114 such that no or very little bacteria are transferred from the perioperative implant cover 100 to the main implantable component 114 during the removal process.

In summary, the removal features of FIGS. 1A-1E, including the retracting cords 132(A) and 132(B) and the opening string 139, allow noninvasive or minimally invasive removal of the perioperative implant cover 100 without contamination of the implant and/or surrounding tissue.

Figure 1F:
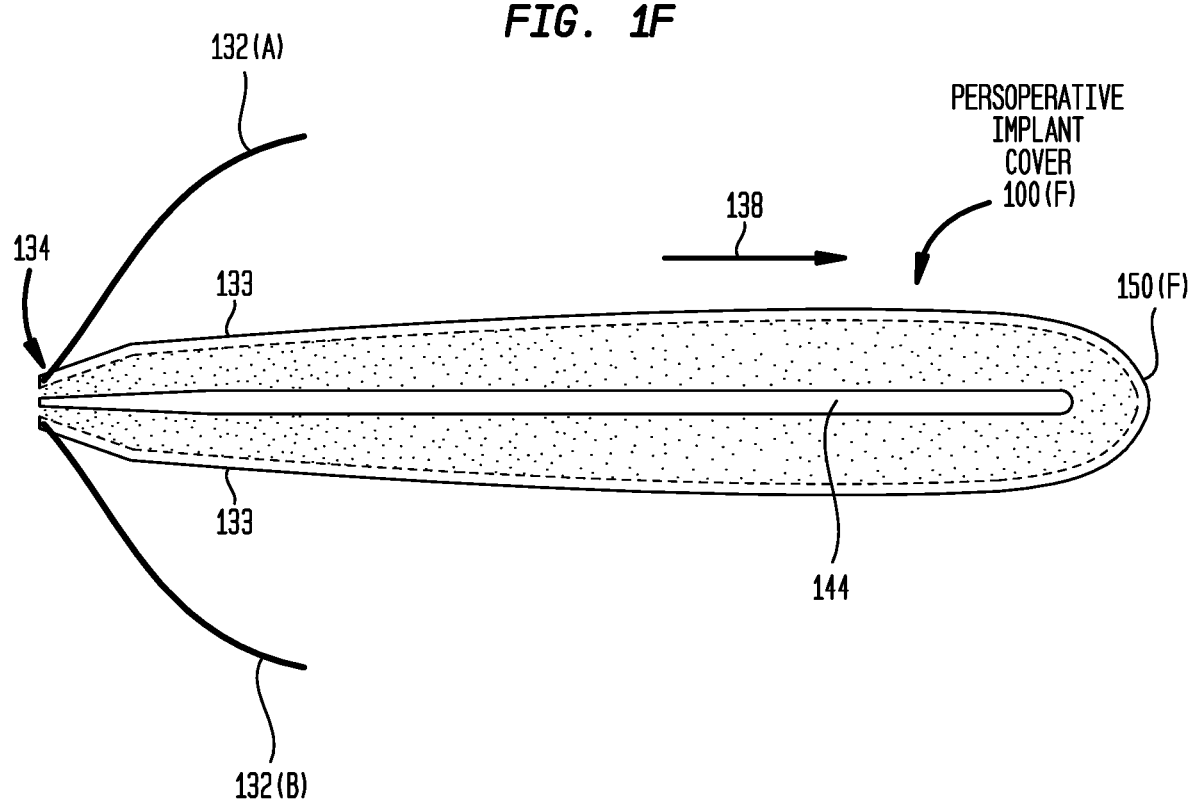
FIG. 1F is a side view of another a perioperative implant cover in accordance with embodiments of the present invention.
Figure 1G:
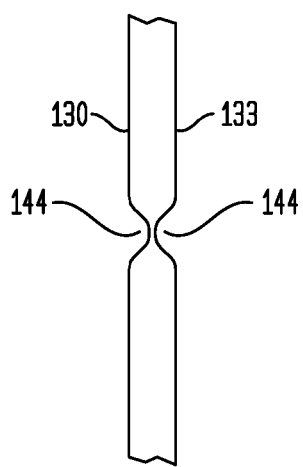
FIG. 1G is a cross-sectional view of a portion of the perioperative implant cover of FIG. 1F.

As noted, FIGS. 1A-1E illustrate one specific arrangement of in situ removal features, including the retracting cords 132(A) and 132(B) and the opening string 139. FIGS. 1F and 1G illustrate further in situ removal features. More specifically, FIGS. 1F and 1G are side and cross-sectional views, respectively, of a portion of a perioperative implant cover 100(F), which is similar to perioperative implant cover 100 of FIGS. 1A-1E. However, in addition to the removal features described above, the perioperative implant cover 100(F) further includes a body 150(F) with in situ removal features in the form of longitudinal mechanical weaknesses 144 extending along a longitudinal length of the perioperative implant cover body 150(F). For ease of illustration, perioperative implant cover 100(F) is shown without main implantable component 114.

The longitudinal mechanical weakness 144 are configured to break/tear, when the distal end 134 of the perioperative implant cover body 150(F) is pulled in direction 138. This tearing at the mechanical weaknesses 144 further enhances the ability of the perioperative implant cover body 150(F) to fold back upon itself during the removal process.

FIGS. 1F and 1G illustrate longitudinal mechanical weaknesses 144 formed by a thinned section of the perioperative implant cover body 150(F). However, it is to be appreciated that the mechanical weaknesses may have other arrangements. It is also to be appreciated that perioperative implant covers may include lateral mechanical weaknesses extending laterally across the cover body at selected locations in addition to, or instead of, longitudinal mechanical weaknesses. The use of lateral mechanical weaknesses may further enhance the ability of the perioperative implant cover body to fold back upon itself during the removal process.

It is also to be appreciated that further in situ features may be used as part of a perioperative implant cover in accordance with embodiments of the present invention. For example, in one embodiment, the retracting cord may be replaced by a pull tab appropriate for finger gripping, or surgical tool gripping to allow pulling off of the cover.

As noted above, the perioperative implant cover body 150 includes a first surface 130 that collects bacteria during the implantation process. In accordance with examples presented herein, the first surface 130 is highly attractive to bacteria so that local bacteria are drawn to, and trapped at, the first surface 130 for removal with the perioperative implant cover 100. In certain examples, the first surface 130 includes a bacteria-attracting coating, such as an ionic coating, or a coating, such as a peptide, silver, multispectrum, antimicrobial, antibiotic, etc. coating, that is intended to kill bacteria, but which is harmless to surrounding cells. In further examples, the first surface 130 includes a surface pattern to increase bacteria attachment and render the area more sterile upon removal. For example, surface geometry on the macro scale may harbor bacteria. The surface may have a roughness that is greater than 0.4 roughness average (Ra) and/or patterns of approximately rectangular surface extrusions that have an aspect ratio of less than one (1) may be utilized. It is to be appreciated that these surface patterns are illustrative and other surface patterns may be used in accordance with embodiments presented herein (e.g., straight edges or changes in topography, channels, a ridged surface on a scale of 10-1000 um, etc.). In certain examples, the first surface 130 may be further configured to be ultralow fouling and/or designed so that surrounding cells, such as mammalian cells, do not adhere to the first surface 130 (i.e., prevent the cover from integrating with host tissue).

In general, the perioperative implant cover 100 is extremely thin so as not to affect the profile of the main implantable component 114 or the size of the surgical "pocket" in which the main implantable component 114 is implanted. The perioperative implant cover body 150 is made from a tear resistant material that is strong while remaining very pliable to allow atraumatic removal from the recipient. For example, the perioperative implant cover body 150 may be formed from a number of different biocompatible polymers such as Polyurethane, PVC, PVA, PEG, Nylon, PET, PTFE, ePTFE, etc.

FIGS. 1A-1G illustrate arrangements in which perioperative implant covers substantially cover a main implantable component 114, including both the skin-facing surface 129 and the bone-facing surface 131 of the main implantable component 114. However, it is to be appreciated perioperative implant covers in accordance with embodiments presented herein may cover different portions of the implantable component 114 and may have different arrangements than that shown in FIGS. 1A-1G.

Figure 2B:
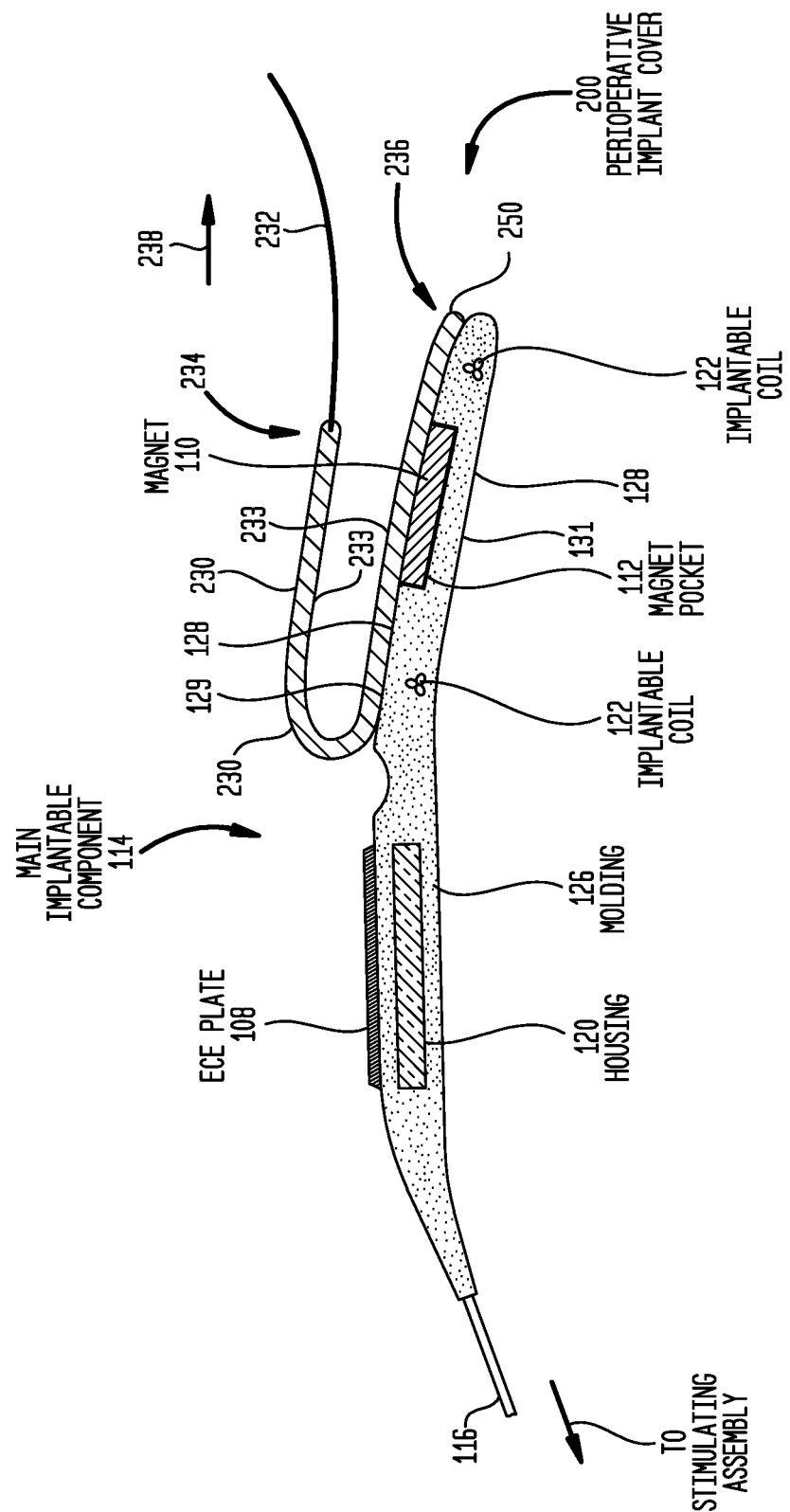
FIG. 2B is a cross-sectional side view of the perioperative implant cover of FIG. 2A during removal of the cover from the cochlear implant.

For example, FIGS. 2A and 2B are diagrams illustrating an arrangement in which a perioperative implant cover 200 covers only the skin-facing surface 129 of the main implantable component 114. In particular, FIG. 2A is a cross-sectional side view of the perioperative implant cover 200 shown with main implantable component 114, while FIG. 2B is a cross-sectional side view of the perioperative implant cover 200 during removal of the cover from the main implantable component 114. Again, for ease of illustration, the recipient's skull and skin/tissue have been omitted from FIGS. 2A and 2B.

As noted, the perioperative implant cover 200 is configured to cover the skin-facing surface 129 of the main implantable component 114 while the main implantable component is implanted in the recipient. More specifically, the perioperative implant cover 200 includes a body 250 having first surface 230. The first surface 230 is attached to the skin-facing surface 129 of the main implantable component 114 so that the perioperative implant cover body 250 remains on the skin-facing surface 129 during implantation of the main implantable component 114 into the recipient. The first surface 230 of perioperative implant cover body 250 may be attached to the skin-facing surface 129 in a manner as described above with reference to FIGS. 1A-1C (e.g., by the elastic nature of the perioperative implant cover, an adhesive surface interactions, etc.).

Once the main implantable component 114 is implanted in the recipient, the perioperative implant cover 200 is configured for removal from the main implantable component 114 and the recipient. To enable removal of the perioperative implant cover 200 either at the end of the intraoperative phase or during the postoperative phase, the perioperative implant cover includes one or more in situ removal features. FIGS. 2A and 2B illustrate an example in which the one or more removal features include a draw cord 232 that is mechanically coupled to (e.g., attached to, embedded in, etc.) a distal end 234 of the perioperative implant cover body 250. In the this example, the distal end 234 is the end of the perioperative implant cover body 250 that is located farthest away from a percutaneous opening (not shown) through which the perioperative implant cover 200 is to be withdrawn from the recipient, while a proximal end 236 of the cover body 250 is the end that is located closest to the percutaneous opening.

When it is time to remove the perioperative implant cover 200 from the cochlear implant 102, a medical practitioner (e.g., surgeon) pulls the retracting cords 232 in the direction illustrated in FIGS. 2A and 2B by arrows 238. This pulling action exerts a force at the distal end 234 of the perioperative implant cover body 250 that causes the first surface 230 of the cover body to peel away from the skin-facing surface 129 of the main implantable component 114. As the distal end 234 of the perioperative implant cover 200 is pulled in direction 238, the proximal end 236 of the cover body 250 remains stationary and attached to the main implantable component 114 until the rest of the cover body 250 is removed, at which time the end 236 also detaches from implantable component 114.

In certain examples, the material properties of the perioperative implant cover body 250 (e.g., the type of material and the thickness of the cover), coupled with the fact that the proximal end 236 remains stationary, causes the perioperative implant cover body 250 to fold back over itself during removal. In other words, during the removal process, the first surface 230 becomes an outward facing surface, while different portions of second surface 233 approach one another. As a result, any surface adhered bacteria on second surface 233 are trapped within the perioperative implant cover body 250 between adjacent portions of the second surface 233 and are withdrawn from the recipient along with the cover.

As noted, the structure of the perioperative implant cover 200 is such that the cover can fold back on itself, as shown in FIG. 2B. This ensures substantial protection of the surface of the main implantable component 114 such that no or very little bacteria are transferred from the cover to the main implantable component 114 or the surrounding tissue/body during the removal process.

Certain surface regions of an implantable component may be more susceptible to bacteria colonization than other surface regions. As such, in accordance with certain embodiments, one or more perioperative implant covers may be applied to specific/discrete surface regions that are susceptible to bacteria colonization, such as the ECE plate 108 and/or the magnet pocket 112/magnet 110.

Figure 2C:
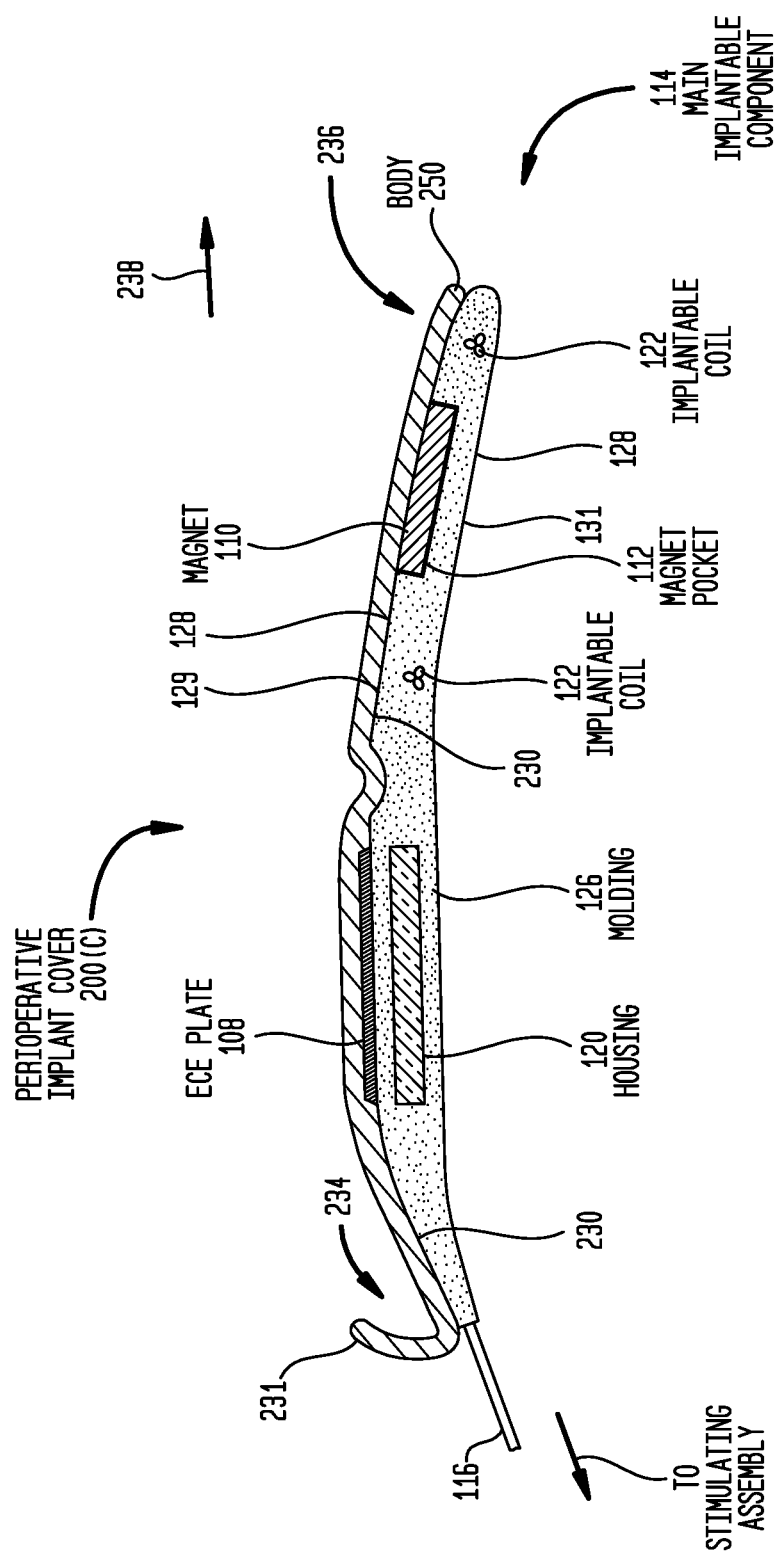
FIG. 2C is a cross-sectional side view of another perioperative implant cover in accordance with embodiments of the present invention shown with a cochlear implant.

As noted above, different in situ removal features may be used as part of a perioperative implant cover in accordance with embodiments of the present invention. For example, FIG. 2C illustrates a perioperative implant cover 200(C) in which the retracting cord 232 may be replaced by a pull tab 231 that is appropriate for finger gripping, or surgical tool gripping to allow pulling off of the cover. As shown in FIG. 2C, the pull tab 231 may be formed from the same material as the cover body 250 (i.e., is an integral extension of the cover body 250). In other embodiments, the pull tab can be formed from a separate material that is attached to the cover body.

FIGS. 3A and 3B illustrate an arrangement where a perioperative implant cover 300 covers a portion of the skin-facing surface 129 of the main implantable component 114, namely the portion of the skin-facing surface 129 that includes the ECE plate 108 and the magnet pocket 112/magnet 110.

In particular, FIG. 3A is a cross-sectional side view of the perioperative implant cover 300 shown with main implantable component 114, while FIG. 3B is a cross-sectional side view of the perioperative implant cover 300 during removal of the cover from the main implantable component 114. Again, for ease of illustration, the recipient's skull and skin/tissue have been omitted from FIGS. 3A and 3B.

Similar to the embodiments of FIGS. 2A-2B, the perioperative implant cover 300 includes a cover body 350. The perioperative implant cover body 350 comprises a first surface 330 that is attached to the skin-facing surface 129 of the main implantable component 114. The first surface 330 is attached such that the perioperative implant cover 300 remains on the skin-facing surface 129 during implantation of the main implantable component 114 into the recipient. The first surface 330 of the perioperative implant cover body 350 may be attached to the skin-facing surface 129 in a manner as described above with reference to FIGS. 1A-1C (e.g., by the elastic nature of the perioperative implant cover, an adhesive surface interactions, etc.).

Once the main implantable component 114 is implanted in the recipient, the perioperative implant cover 300 is configured for removal from the main implantable component 114 and the recipient. To enable removal of the perioperative implant cover 300 either at the end of the intraoperative phase or during the postoperative phase, the perioperative implant cover includes one or more in situ removal features. FIGS. 3A and 3B illustrate an example in which the one or more removal features include a pair of retracting cords 332(A) and 332(B) that are each mechanically coupled to (e.g., attached to, embedded in, etc.) one of the opposing ends 334 and 336 of the perioperative implant cover body 350

In the embodiments of FIGS. 3A and 3B, a percutaneous opening (not shown) through which the perioperative implant cover 300 is to be withdrawn is located generally above a central point of the main implantable component 114. As such, when it is time to remove the perioperative implant cover 300 from the main implantable component 114, a medical practitioner simultaneously pulls the retracting cords 332 in the direction illustrated in FIGS. 3A and 3B by arrows 338. This pulling action exerts forces at the opposing ends 334 and 336 of the perioperative implant cover body 350 that cause the first surface 330 of the cover to peel away from the skin-facing surface 129 at the opposing ends of the main implantable component 114. As the opposing ends 334 and 336 of the perioperative implant cover 300 are pulled in direction 338, a central section 335 of the perioperative implant cover body 350 remains stationary and attached to the main implantable component 114 until the rest of the cover body 350 is removed, at which time the central section 335 also detaches from implantable component 114.

In certain examples, the material properties of the perioperative implant cover body 350 (e.g., the type of material and the thickness of the cover), coupled with the fact that the central section 335 remains stationary, cause the perioperative implant cover 300 to fold back over itself during removal to trap bacteria within the cover during removal. In other words, during the removal process, the first surface 330 becomes an outward facing surface, while different portions of the second surface 333 approach one another. As a result, any surface adhered bacteria on second surface 333 are trapped within the perioperative implant cover 300 itself, namely between adjacent portions of the second surface 333 and are withdrawn from the recipient along with the cover. The structure of the perioperative implant cover 300 is such that it can fold back on itself, as shown in FIG. 3B. This ensures substantial protection of the surface of the main implantable component 114 such that no or very little bacteria are transferred from the cover to the main implantable component 114 during the removal process.

As noted, FIGS. 3A-3B illustrate an example in which the retracting cords 332(A) and 332(B) are pulled substantially simultaneously so that the perioperative implant cover 300 folds towards central section 335. This enables the perioperative implant cover 300 to be withdrawn through the percutaneous opening located generally above a central point of the main implantable component 114. In an alternative embodiment, the retracting cords 332(A) and 332(B) may be pulled at different times relative to one another such that the perioperative implant cover 300 folds in a different direction.

Figure 3C:
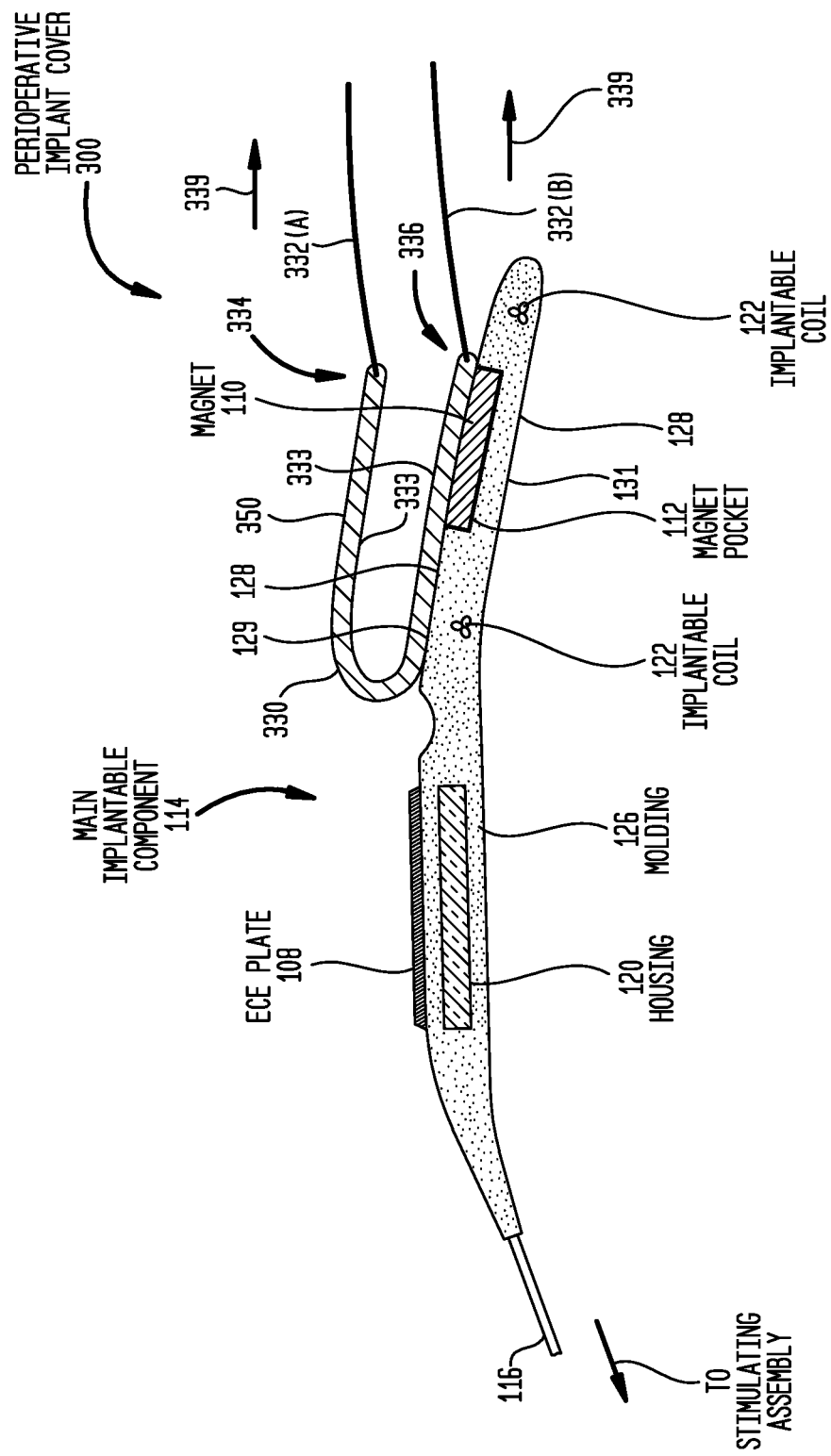
FIG. 3C is a cross-sectional side view of the perioperative implant cover of FIG. 3A illustrating a second technique for removal of the cover from the cochlear implant.

For example, FIG. 3C illustrates the perioperative implant cover 300 during removal through a percutaneous opening that is located near end 336, thus making end 336 a proximal end of the cover body 350 and end 334 a distal end of the cover body 350. In this embodiment, a medical practitioner differentially pulls on retracting cords 332(A) and 332(B) (i.e., pulls at different times) to remove the perioperative implant cover 300.

More specifically, as shown in FIG. 3C, when it is time to remove the perioperative implant cover 300, a medical practitioner initially pulls on retracting cord 332(A) in the general direction shown by arrows 339. This pulling action exerts a force at the distal end 334 of the perioperative implant cover body 350 causes the first surface 330 of the cover body to peel away from the skin-facing surface 129 of the main implantable component 114. As the distal end 334 of the perioperative implant cover body 350 is pulled in direction 339, the proximal end 336 remains stationary and attached to the main implantable component 114 until the rest of the cover body 350 is removed, at which time the end 336 also detaches from implantable component 114.

In certain examples, the material properties of the perioperative implant cover body 350 (e.g., the type of material and the thickness of the cover), coupled with the fact that the proximal end 336 remains stationary, causes the perioperative implant cover body 350 to fold back over itself during removal. In other words, during the removal process, the first surface 330 becomes an outward facing surface, while different portions of second surface 333 approach one another. As a result, any surface adhered bacteria on second surface 333 are trapped within the perioperative implant cover 300 between adjacent portions of the second surface 333 and are withdrawn from the recipient along with the cover.

When the perioperative implant cover 300 is folded such that the distal end 334 of the cover body 350 is positioned adjacent the proximal end 336, the medical practitioner may then begin pulling on retracting cord 332(B) simultaneously with retracting cord 332(A). This simultaneous pulling action causes the distal end 334 to release from the main implantable component 114 and move along with the proximal end 336 as the perioperative implant cover 300 is removed from the recipient, thereby retaining the cover body 350 in a folded arrangement to ensure the trapped bacteria remains inside of the cover.

In the example of FIG. 3C, the retracting cords 332(A) and 332(B) are operated separately in order to remove the cover body 350. In an alternative example, the first retracting cord 332(A) has knot/stopper located thereon and retracting cord 332(B) has a loop therein. A distal end of the retracting cord 332(A) passes through the loop, but the knot/stopper cannot pass through the loop. In such an arrangement, a surgeon may remove the whole cover body in a manner determined by the location of the knot/stopper by pulling only retracting cord 332(A).

FIGS. 1A to 3C illustrate various arrangements for perioperative implant covers used with the main implantable component 114 of a cochlear implant 102. However, it is to be appreciated that perioperative implant covers in accordance with embodiments of the present invention may be used to cover other discrete sections of a cochlear implant (e.g., the lead region, only the magnet pocket, etc.), or other implantable components, such as bone conduction devices, mechanical stimulators, implantable cardioverter defibrillators (ICDs), implantable pacemakers, functional electrical stimulation devices or other neurostimulators, pain management implants, implantable drug or insulin pumps, mammary prosthesis/breast implants, cosmetic or reconstructive implants and prosthetics, etc.

Figure 4:
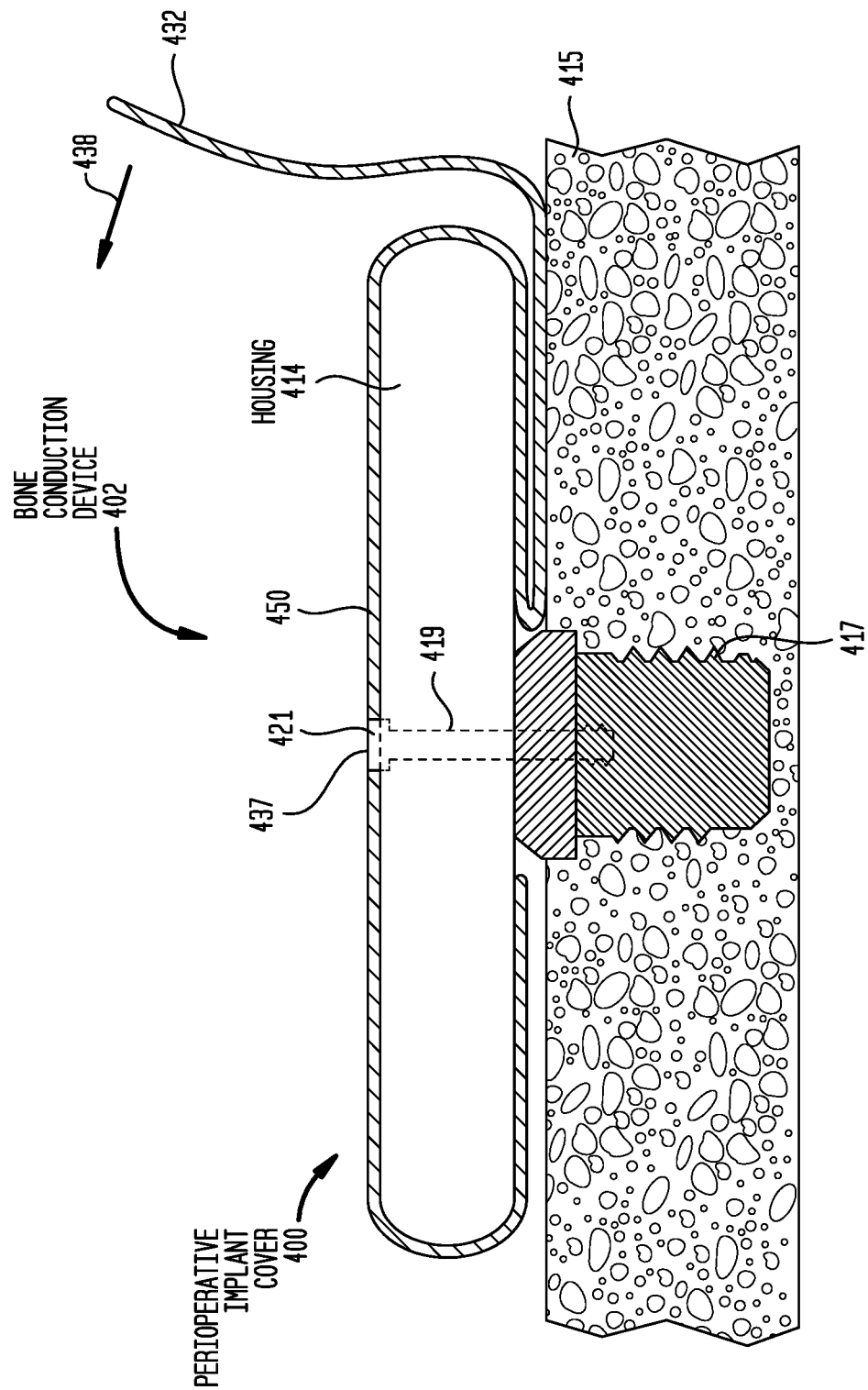
FIG. 4 is a cross-sectional side view of a perioperative implant cover in accordance with embodiments of the present invention shown with a bone conduction device.
Figure 5:
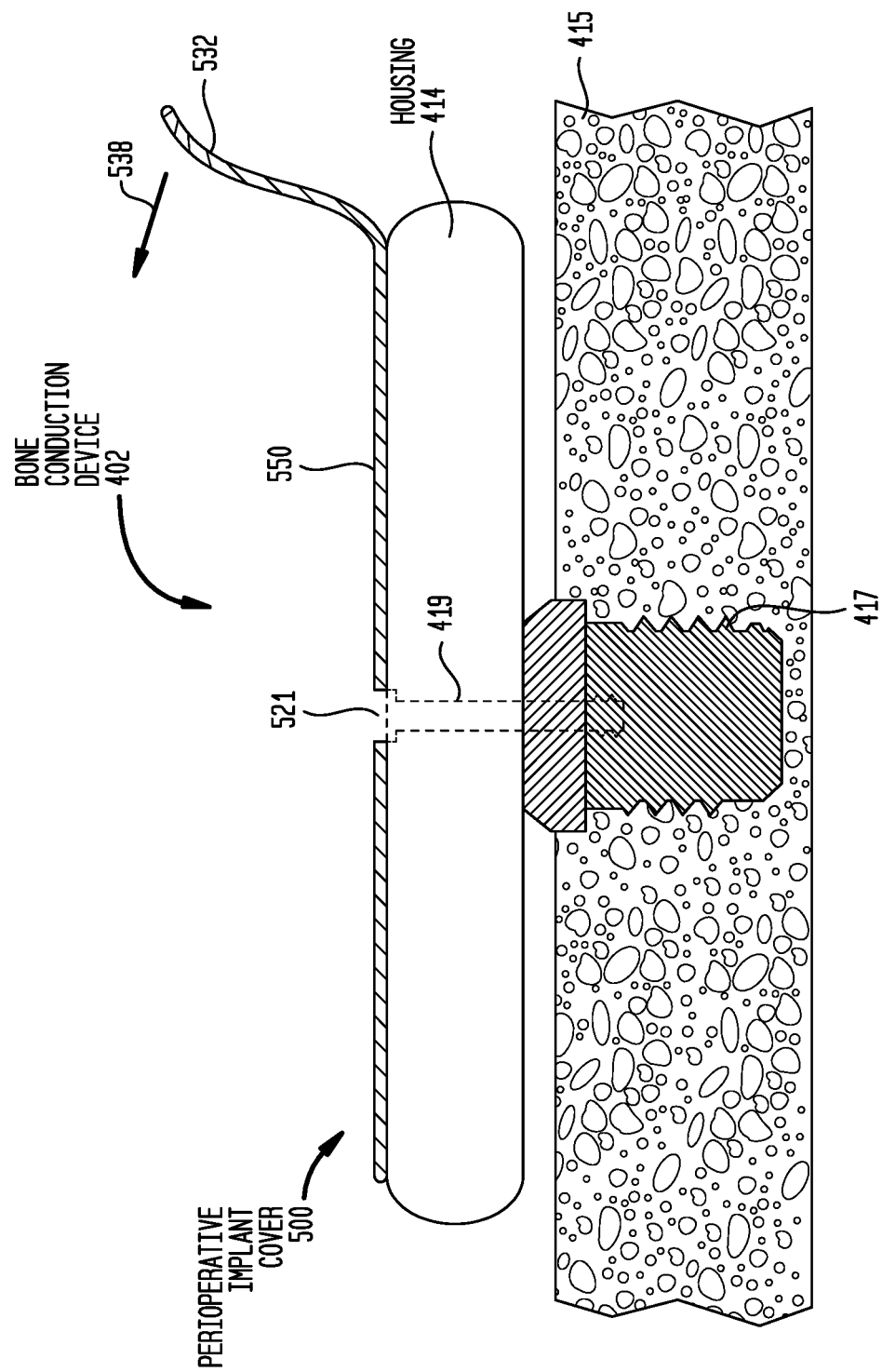
FIG. 5 is a cross-sectional side view of another perioperative implant cover in accordance with embodiments of the present invention shown with a bone conduction device.

FIGS. 4 and 5 are diagrams illustrating perioperative implant covers in accordance with embodiments of the present invention for use with an implantable component of a bone conduction device 402. Referring first to FIG. 4, the bone conduction device 402 includes a housing 414 that is secured to the recipient's skull bone 415 via a bone screw 417. During implantation, the bone screw 417 is implanted in the recipient's skull 415 and the housing 414 is then subsequently attached to the bone screw via a fixation screw 419. The housing 414 may include a variety of different operational components, such as an actuator, battery, transceiver, etc., depending on the type and configuration of the bone conduction device 402.

The perioperative implant cover 400 is configured to cover at least a portion of the housing 414 while the housing is implanted in the recipient. In the specific examples of FIG. 4, the perioperative implant cover 400 includes a cover body 450 is in the form of a sheath or pouch that substantially surrounds the housing 414. The perioperative implant cover body 450 includes an aperture 421 that enables attachment of the fixation screw 419. In certain examples, the aperture 421 may be optionally closed by a flap 437 that can be opened to allow interaction with the fixation screw 419.

To enable removal of the perioperative implant cover 400, the perioperative implant cover includes one or more in situ removal features. FIG. 4 illustrates an example in which the removal features include a removal tab 432. When it is time to remove the perioperative implant cover 400 from the housing 414, a medical practitioner (e.g., surgeon) pulls the removal tab 432 away from the housing (e.g., in the general direction illustrated in FIG. 4 by arrow 438). This pulling action exerts a force so as to peel the perioperative implant cover body 450 from the housing 414.

FIG. 5 illustrates an arrangement in which a perioperative implant cover 500 includes a cover body 550 that covers only a skin-facing surface of the housing 414 of bone conduction device 402. Similar to the arrangement of FIG. 4, the perioperative implant cover 500 includes a removal tab 532. When it is time to remove the perioperative implant cover body 550 from the housing 414, a medical practitioner (e.g., surgeon) pulls the removal tab 532 away from the housing (e.g., in the general direction illustrated in FIG. 5 by arrow 538). This pulling action exerts a force so as to peel the perioperative implant cover body 550 from the housing 414. The perioperative implant cover body 550 also includes an aperture 521 that enables attachment of the fixation screw 419.

FIGS. 4 and 5 illustrate example perioperative implant covers for use with a bone conduction device. However, it is to be appreciated that the various embodiments presented herein are not mutually exclusive. As such, the perioperative implant covers of FIGS. 4 and 5 may also or alternatively include in situ removal features as above with reference to FIGS. 1A-3C (e.g., retracting cords, an opening string, mechanical weaknesses, etc.).

FIG. 6 is a flowchart of a method 600 in accordance with embodiments of the present invention. Method 600 begins at 602 where an implantable component of an implantable medical device is implanted into a recipient while a perioperative implant cover comprising a body is disposed on at least a portion of a surface of the implantable component during implantation of the implantable component into the recipient. At 604, the perioperative implant cover is removed from the recipient after the implantable component is fully implanted in the recipient. In certain examples, the perioperative implant cover is removed through a percutaneous opening in the recipient's skin.

In accordance with one embodiment of the method of FIG. 6, removing the perioperative implant cover from the recipient comprises actuating at least one retracting cord to separate the body of the perioperative implant cover from the surface of the implantable component. In accordance with a further embodiment, the perioperative implant cover further comprises an opening string disposed around an aperture in the body of the perioperative implant cover and mechanically connected to two or more retracting cords. In such embodiments, removing the perioperative implant cover from the recipient comprises actuating the two or more retracting cords to place an opening force on the opening string to increase the size of the aperture in the body of the perioperative implant cover.

In accordance with certain embodiments of FIG. 6, removing the perioperative implant cover from the recipient further comprises actuating at least one retracting cord to cause the body of the perioperative implant cover to fold back over itself during separation from the implantable component.

Embodiments of the present invention have been described with reference to removal of perioperative implant covers through a percutaneous opening in a recipient's skin tissue (e.g., incision, cannula, etc.). However, in an alternative embodiment, the perioperative implant covers may be removed through the recipient's ear or Eustachian tube. For example, in the examples of FIGS. 1A-1E, the retracting cords 132(A) and 132(B) may extend through the middle ear and out of a tympanostomy/grommet, thereby enabling the cover to be withdrawn through the recipient's ear. Alternatively, ontological instruments could be used to retrieve the cover via the middle ear cavity.

Embodiments of the present invention have been primarily described with reference to perioperative implant covers used with implantable hearing prostheses, such as cochlear implants and bone conduction devices. As noted elsewhere herein, perioperative implant covers in accordance with embodiments of the present invention may have various shapes and configurations for use with other implantable components, such as mechanical stimulators, implantable cardioverter defibrillators (ICDs), implantable pacemakers, functional electrical stimulation devices or other neurostimulators, pain management implants, implantable drug or insulin pumps, mammary prosthesis/breast implants, cosmetic or reconstructive implants and prosthetics, etc. FIG. 7 is a cross-sectional side view of a perioperative implant cover 700 in accordance with embodiments of the present invention shown with a pacemaker.

More specifically, FIG. 7 illustrates a pacemaker can/housing 714 with wires 718 extending to a pacing lead (not shown). The pacemaker housing 714 and the pacing lead are configured to be implanted within a recipient. As described further below, the perioperative implant cover 700 is attached to the pacemaker housing 714 before implantation, and is configured to remain attached thereto during the implantation surgery.

The perioperative implant cover 700 has a body 750 that is configured to cover at least a portion of the pacemaker housing 714 during implantation of the housing in the recipient. In the examples of FIG. 7, the pacemaker housing 714 includes an outer surface 728 and the perioperative implant cover body (cover body) is in the form of a sheath or pouch that substantially surrounds the outer surface 728 of the pacemaker housing 714.

More specifically, the cover body 750 includes a first surface 730 (e.g., an interior or device-facing surface) that defines an interior cavity in which the pacemaker housing 714 is positioned. The first surface 730 is attached to the outer surface 728 of the pacemaker housing 714. In general, the first surface 730 is attached to the outer surface 728 of the pacemaker housing 714 such that cover body 750 remains on the outer surface during implantation of the pacemaker housing 714 into the recipient. In certain embodiments, the first surface 730 is attached to the outer surface 728 as a result of the elastic nature of the cover material and/or by being close fitting/confirming to the shape of the pacemaker housing 714. In further embodiments, the first surface 730 of the perioperative implant cover body 750 is attached to the outer surface 728 via an adhesive (e.g., silicone adhesive) or hook-and-loop fasteners. In other examples, the first surface 730 is attached to the outer surface 728 through surface interactions (e.g., friction). In certain such examples, the first surface 730 may be textured (e.g., include dimples/protrusions, ridges, concavities, etc.) to increase the friction between the first surface 730 and the outer surface 728.

In further embodiments, features of the pacemaker housing 714 may be used to retain the body 750 of the perioperative implant cover 700 on the pacemaker housing and/or a magnet may be disposed in the cover body 750. In one such embodiment, the magnet in the perioperative implant cover body 750 is magnetically coupled to the pacemaker housing 714 to retain the position of the cover during implantation.

In certain embodiments, the perioperative implant cover 700 (i.e., the cover body 750) is attached to the pacemaker housing 714 during, for example, a manufacturing process. As such, the perioperative implant cover 700 may be attached in a controlled and sterile environment to ensure that no bacteria are sealed between the cover and the pacemaker housing 714. In such examples, the pacemaker housing 714 and attached perioperative implant cover 700 may then be packaged together in sterile packaging material. Alternatively, the perioperative implant cover 700 may be attached to the pacemaker housing 714 prior to, or at the beginning of an implantation surgery in a sterile manner or in a sterile field.

As noted above, once the pacemaker housing 714 is implanted in the recipient at its final position/location, the perioperative implant cover 700 is configured for removal from the main pacemaker housing 714 (and the recipient) in a manner that eliminates or reduces the transfer of bacteria from the cover to the pacemaker housing 714. That is, the perioperative implant cover 700 includes one or more structural features that enable a medical practitioner (e.g., surgeon) to separate the cover from the pacemaker housing 714 and withdraw the cover from the recipient without transferring bacteria from the perioperative implant cover 700 to the surface of the main pacemaker housing 714.

To enable removal of the perioperative implant cover 700, the perioperative implant cover includes one or more in situ removal features that enable the perioperative implant cover 700 to be removed from the pacemaker housing 714 and the recipient at end of the implantation surgery, namely either as final step, or one of the final steps, of the intraoperative phase just before the wound is closed or during the postoperative phase, such as three (3) days after the implantation surgery (e.g., percutaneous removal a couple of days after the surgery). This minimizes and/or eliminates a time period during which the surface of the pacemaker housing 714 is exposed to any bacteria present in the surgical theater.

In accordance with examples presented herein in which the perioperative implant cover 700 is removed during the postoperative phase, no second surgery is envisaged. Instead, the perioperative implant cover 700 may be withdrawn through a percutaneous opening (e.g., a fistula/cannula or small incision) remote from the implantable component.

A perioperative implant cover in accordance with embodiments of the present invention may include a number of different removal features in various combinations. FIG. 7 illustrates an arrangement in which the removal features include two percutaneous draw or retracting cords/strings 732(A) and 732(B) that are each mechanically coupled to (e.g., attached to, embedded in, etc.) a distal portion 734 of the perioperative implant cover body 750.

The retracting cords 732(A) and 732(B) may have different arrangements and may be formed from, for example, metal, polymers, etc. For example, the retracting cords 732(A) and 732(B) may be percutaneous elements (i.e., elements that extend through the percutaneous removal opening) or may be subcutaneous elements (i.e., elements that terminate subcutaneously for subsequent retrieval by the medical practitioner). In certain examples, the retracting cords 732(A) and 732(B) may have a radiopaque marker that is externally detectable by, for example, medical imaging techniques (e.g., X-ray, Ultraviolet (UV), infrared (IR), etc.). In further examples, the retracting cords 732(A) and 732(B) may be impregnated or coated with a non-fouling material, an antibacterial material, biocide, etc. The retracting cords 732(A) and 732(B) may be formed from a different material than the cover body 750 or may be continuations of the material forming the cover body 750. Additionally, the retracting cords 732(A) and 732(B) may be coated wires or wire coated strings.

As described elsewhere herein, the retracting cords 732 (A) and 732(B) are used to remove the perioperative implant cover 700 through a percutaneous removal opening. The percutaneous removal opening may be an incision in the recipient's skin tissue, or an opening formed by a withdrawal tube/cannula extending through the recipient's skin tissue. Such a withdrawal tube may be formed, for example, from metal or a hard thermoplastic, or may be a relatively soft material through which the retracting cords 732(A) and 732(B) and perioperative implant cover 700 may be withdrawn.

When it is time to remove the perioperative implant cover 700 from the pacemaker housing 714, a medical practitioner (e.g., surgeon) pulls the retracting cords 732(A) and 732(B) towards the percutaneous opening (i.e., in the general direction illustrated in FIG. 7 by arrow 738). The actuation (pulling action) of the retracting cords 732(A) and 732(B) exerts a force on an opening string 739 that is mechanically connected to the retracting cords 732(A) and 732(B). As such, the opening string 739 is disposed around an aperture 740 located in the distal portion 734 of the perioperative implant cover body 750. When the medical practitioner (e.g., surgeon) actuates (pulls) the retracting cords 732(A) and 732(B) towards the percutaneous opening, the retracting cords in turn place an opening (pulling) force on the opening string 739 to increase the size of the aperture 740. The increased aperture size enables the cover body 750 to be pulled back over the larger geometry of the pacemaker housing 714.

After aperture 740 has the increased size, and in response to additional force on the retracting cords 732(A) and 732(B), the first surface 730 of the cover body 750 peels away from the outer surface 728 of the pacemaker housing 714. As the distal portion 734 of the perioperative implant cover body 750 is pulled in direction 738, a proximal portion 736 remains stationary and attached to the pacemaker housing 714 until the rest of the cover body 750 is removed, at which time the proximal end 736 also detaches from pacemaker housing 714.

The perioperative implant cover body 750 has a structure (e.g., formed from type of material, a thickness, etc.) that, when coupled with the fact that the proximal portion 736 remains stationary, causes the perioperative implant cover body 750 to fold back over itself during removal. In other words, during the removal process, the first surface 730 becomes the outward facing surface, while different portions of a second surface (e.g., initially outer or outward-facing) surface 733 of the cover body 750 approach one another. As a result, any surface adhered bacteria on outer surface 733 are trapped within the perioperative implant cover body 750 between adjacent portions of the outer surface 733 and are withdrawn from the recipient along with the cover body 750. This ensures substantial protection of the surface of the main pacemaker housing 714 such that no or very little bacteria are transferred from the perioperative implant cover 700 to the pacemaker housing 714 during the removal process.

In summary, the removal features of FIG. 7, including the retracting cords 732(A) and 732(B) and the opening string 739, allow noninvasive or minimally invasive removal of the perioperative implant cover 700 without contamination of the implant and/or surrounding tissue.

As noted, FIG. 7 illustrates one specific arrangement of in situ removal features, including the retracting cords 732(A) and 732(B) and the opening string 739. It is to be appreciated that other removal features described elsewhere herein (e.g., mechanical weaknesses, pull tabs, etc.), may also or alternatively be used in the examples of FIG. 7.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device system, comprising:
    an implantable component for implantation into a recipient, wherein the implantable component is a component of a cochlear implant; and
    a perioperative implant cover comprising a body disposed on at least a portion of a surface of the implantable component during implantation of the implantable component into the recipient,
    wherein the perioperative implant cover includes one or more in situ removal features including at least one retracting cord attached to a portion of the body of the perioperative implant cover enabling the perioperative implant cover to be removed from the surface of the implantable component after implantation in the recipient,
    wherein the body of the perioperative implant cover is configured to fold back over itself during removal from the implantable component.

2. The implantable medical device system of claim 1, wherein the at least one retracting cord comprises two or more retracting cords, and wherein the one or more in situ removal features further comprise:
    an opening string disposed around an aperture in the body of the perioperative implant cover and mechanically connected to the two or more retracting cords such that actuation of the retracting cords places an opening force on the opening string to increase a size of the aperture in the body of the perioperative implant cover.

3. The implantable medical device system of claim 1, wherein the one or more in situ removal features further comprise:
    at least one removal tab extending from the body of the perioperative implant cover.

4. The implantable medical device system of claim 1, wherein the one or more in situ removal features further include:
    one or more mechanical weaknesses in the body of the perioperative implant cover.

5. The implantable medical device system of claim 1, wherein the body of the perioperative implant cover is a sheath configured to substantially surround the implantable component.

6. The implantable medical device system of claim 1, wherein the body of the perioperative implant cover includes an outer surface that is configured to attract bacteria.

7. The implantable medical device system of claim 6, wherein the outer surface of the body of the perioperative implant cover includes a bacteria-attracting coating.

8. The implantable medical device system of claim 6, wherein the outer surface of the body of the perioperative implant cover includes a surface pattern to attract bacteria.

9. A method, comprising:

implanting an implantable component of a cochlear implant into a recipient, wherein a perioperative implant cover, which comprises a body and one or more in situ removal features, is disposed on at least a portion of a surface of the implantable component during implantation of the implantable component into the recipient, wherein the one or more in situ removal features include at least one of a retracting cord attached to a portion of the body; and removing, with the at least one retracting cord, the perioperative implant cover cover from the recipient after the implantable component is fully implanted in the recipient, wherein the body of the perioperative implant cover is configured to fold back over itself during removal from the implantable component.

10. The method of claim 9, wherein removing the perioperative implant cover from the recipient after the implantable component is fully implanted in the recipient comprises:

removing, with the at least the retracting cord, the perioperative implant cover through a percutaneous opening in skin of recipient.

11. The method of claim 9, wherein removing the perioperative implant cover from the recipient after the implantable component is fully implanted in the recipient comprises:

actuating the at least one retracting cord to separate the body of the perioperative implant cover from the surface of the implantable component.

12. The method of claim 11, wherein the at least one retracting cord comprises two or more retracting cords, and wherein the perioperative implant cover further comprises an opening string disposed around an aperture in the body of the perioperative implant cover and mechanically connected to the two or more retracting cords, the method further comprising:

actuating the two or more retracting cords to place an opening force on the opening string to increase a size of the aperture in the body of the perioperative implant cover.

13. The method of claim 11, further comprising:

actuating the at least one retracting cord to cause the body of the perioperative implant cover to fold back over itself during separation from the implantable component.

14. An implantable medical device system, comprising:

an implantable component for implantation into a recipient, wherein the implantable component is a component of a bone conduction device; and a perioperative implant cover comprising a body disposed on at least a portion of a surface of the implantable component during implantation of the implantable component into the recipient, wherein the perioperative implant cover includes one or more in situ removal features including at least one retracting cord attached to a portion of the body of the perioperative implant cover enabling the perioperative implant cover to be removed from the surface of the implantable component after implantation in the recipient, wherein the body of the perioperative implant cover is configured to fold back over itself during removal from the implantable component.

15. The implantable medical device system of claim 14, wherein the at least one retracting cord comprises two or more retracting cords, and wherein the one or more in situ removal features further comprise:

an opening string disposed around an aperture in the body of the perioperative implant cover and mechanically connected to the two or more retracting cords such that actuation of the retracting cords places an opening force on the opening string to increase a size of the aperture in the body of the perioperative implant cover.

16. The implantable medical device system of claim 14, wherein the one or more in situ removal features further comprise:

at least one removal tab extending from the body of the perioperative implant cover.

17. The implantable medical device system of claim 14, wherein the one or more in situ removal features further include:

one or more mechanical weaknesses in the body of the perioperative implant cover.

18. The implantable medical device system of claim 14, wherein the body of the perioperative implant cover is a sheath configured to substantially surround the implantable component.

19. The implantable medical device system of claim 14, wherein the body of the perioperative implant cover includes an outer surface that is configured to attract bacteria.

20. The implantable medical device system of claim 19, wherein the outer surface of the body of the perioperative implant cover includes a bacteria-attracting coating.

21. The implantable medical device system of claim 19, wherein the outer surface of the body of the perioperative implant cover includes a surface pattern to attract bacteria.

22. An implantable medical device system, comprising:

an implantable component for implantation into a recipient; and a perioperative implant cover comprising a body disposed on at least a portion of a surface of the implantable component during implantation of the implantable component into the recipient, wherein the perioperative implant cover includes one or more in situ removal features including:

two or more retracting cords attached to a portion of the body of the perioperative implant cover, and an opening string disposed around an aperture in the body of the perioperative implant cover and mechanically connected to the two or more retracting cords such that actuation of the retracting cords places an opening force on the opening string to increase a size of the aperture in the body of the perioperative implant cover, wherein the one or more in situ removal features enable the perioperative implant cover to be removed from the surface of the implantable component after implantation in the recipient, and wherein the body of the perioperative implant cover is configured to fold back over itself during removal from the implantable component.

23. The implantable medical device system of claim 22, wherein the one or more in situ removal features further comprise:

at least one removal tab extending from the body of the perioperative implant cover.

24. The implantable medical device system of claim 22, wherein the one or more in situ removal features further include:

one or more mechanical weaknesses in the body of the perioperative implant cover.

25. The implantable medical device system of claim 22, wherein the body of the perioperative implant cover is a sheath configured to substantially surround the implantable component.

26. The implantable medical device system of claim 22, wherein the body of the perioperative implant cover includes an outer surface that is configured to attract bacteria.

27. The implantable medical device system of claim 26, wherein the outer surface of the body of the perioperative implant cover includes a bacteria-attracting coating.

28. The implantable medical device system of claim 26, wherein the outer surface of the body of the perioperative implant cover includes a surface pattern to attract bacteria.

29. The implantable medical device system of claim 22, wherein the implantable component is a component of a cochlear implant.

30. The implantable medical device system of claim 22, wherein the implantable component is a component of a bone conduction device.

31. A method, comprising:
    implanting an implantable component of a bone conduction device into a recipient, wherein a perioperative implant cover, which comprises a body and one or more in situ removal features, is disposed on at least a portion of a surface of the implantable component during implantation of the implantable component into the recipient, wherein the one or more in situ removal features include at least one retracting cord attached to a portion of the body; and
    removing, with the at least retracting cord, the perioperative implant cover from the recipient after the implantable component is fully implanted in the recipient, wherein the body of the perioperative implant cover is configured to fold back over itself during removal from the implantable component.

32. The method of claim 31, wherein removing the perioperative implant cover from the recipient after the implantable component is fully implanted in the recipient comprises:
    removing, with the at least one of the retracting cord, the perioperative implant cover through a percutaneous opening in skin of the recipient.

33. The method of claim 31, wherein removing the perioperative implant cover from the recipient after the implantable component is fully implanted in the recipient comprises:
    actuating the at least one retracting cord to separate the body of the perioperative implant cover from the surface of the implantable component.

34. The method of claim 33, wherein the at least one retracting cord comprises two or more retracting cords, and wherein the perioperative implant cover further comprises an opening string disposed around an aperture in the body of the perioperative implant cover and mechanically connected to the two or more retracting cords, the method further comprising:
    actuating the two or more retracting cords to place an opening force on the opening string to increase a size of the aperture in the body of the perioperative implant cover.

35. The method of claim 31, wherein removing the perioperative implant cover from the recipient after the implantable component is fully implanted in the recipient comprises:
    actuating the at least one retracting cord to separate the body of the perioperative implant cover from the surface of the implantable component.

36. The method of claim 31, further comprising:
    actuating the at least one retracting cord to cause the body of the perioperative implant cover to fold back over itself during separation from the implantable component.

* * * * *

UNITED STATES PATENT AND TRADEMARK OFFICE
CERTIFICATE OF CORRECTION

PATENT NO. : 10,537,743 B2
APPLICATION NO. : 15/158136
DATED : January 21, 2020
INVENTOR(S) : Smyth et al.

Page 1 of 1

It is certified that error appears in the above-identified patent and that said Letters Patent is hereby corrected as shown below:

In the Claims

Column 19, Line 11, remove "cover" after "perioperative implant cover".

Signed and Sealed this
Twenty-third Day of June, 2020

Andrei Iancu
*Director of the United States Patent and Trademark Office*